United States Patent [19]
Oin

[11] Patent Number: 5,869,040
[45] Date of Patent: Feb. 9, 1999

[54] GENE THERAPY METHODS AND COMPOSITIONS

[75] Inventor: Xiao-Oiang Oin, Brighton, Mass.

[73] Assignee: Biogen, Inc, Cambridge, Mass.

[21] Appl. No.: 481,814

[22] Filed: Jun. 7, 1995

[51] Int. Cl.$^6$ .................................................. A01N 63/00
[52] U.S. Cl. .................. 424/93.21; 435/69.1; 435/320.1; 435/366; 536/23.5
[58] Field of Search .............................. 435/172.3, 240.1, 435/240.2, 252.2, 252.3, 320.1, 6, 69.7, 69.1, 366; 536/24.1, 24.31, 27, 23.5; 514/44; 424/93.21

[56] References Cited

U.S. PATENT DOCUMENTS

| | | | |
|---|---|---|---|
| 4,797,368 | 1/1989 | Carter et al. | 435/320.1 |
| 5,139,941 | 8/1992 | Muzyczka | 435/172.3 |
| 5,264,618 | 11/1993 | Felgner et al. | 560/224 |
| 5,399,346 | 3/1995 | Anderson et al. | 424/93.21 |
| 5,595,884 | 1/1997 | Androphy et al. | 435/69.1 |

FOREIGN PATENT DOCUMENTS

| | | |
|---|---|---|
| A-648 493 | 4/1995 | European Pat. Off. . |
| 2 282 814 | 4/1995 | United Kingdom . |
| WO 91/15580 | 10/1991 | WIPO . |
| WO 93/23539 | 11/1993 | WIPO . |
| WO 94/09160 | 4/1994 | WIPO . |
| WO 94/21115 | 9/1994 | WIPO . |

OTHER PUBLICATIONS

Barinaga, M. 1994 Science 266: 1326.
Marshall, E. 1995 Science 269: 1050–1055.
Crystal, R. 1995 Science 270: 404–410.
Orkin, S.H. et al. 1995 Report and Recommendations of the Panel to Assess the NIH Investment in Research on Gene Therapy.
Herskowitz, I. 1987 Nature 329: 219–222.
Ransone, L. et al. 1990 Proc. Nat'l Acad. Sci USA 87: 3806–3810.
Johnson et al. 1994 Proc. Nat'l Acad. Sci USA 91: 12823–12827.
Helin et al. 1992 Cell 70: 337–350.
Flotte and Carter, "Adeno–associated virus vectors for gene therapy", (1995) Gene Therapy 2, 357–362.
Xiao, Li and Samulski, "Efficient Long–Term Gene Transfer into Muscle Tissue of Immunocompetent Mice by Adeno–Associated Virus Vector", (1996) Journal of Virology, 70, 8089–8108.
Kaplitt, Leone, Samulski, Xiao, Pfaff, O'Malley and During, "Long–term gene expression and phenotypic correction using adeno–associated virus vectors in the mammalian brain", (1994) Nature Genetics 8, 148–153.
Flotte et al., "Stable in vivo expression of the cystic fibrosis transmembrane conductance regulator with an adeno–associated virus vector", (Proc. Natl. Acad. Sci. USA (1993) 90, 10613–10617.
Fisher et al. "Recombinant adeno–associated virus for muscle directed gene therapy", (Nature Medicine (1997) 3, 306–312.

Kessler et al., "Gene delivery to skeletal muscle results in sustained expression and systemic delivery of a therapeutic protein", (Proc. Natl. Acad. Sci. USA (1996)93, 14082–14087.
Okada et al., "Gene therapy against an experimental glioma using adeno–associated virus vectors", (1996) Gene Therapy 3, 957–964.
Clayman et al., "In Vivo Molecular Therapy with p53 Adenovirus for Microscopic Residual Head and Neck Squamous Carcinoma", (1995) Cancer Research 55, 1–6.
Hirschowitz et al., "In Vivo Adenovirus–Mediated Gene Transfer of the *Escherichia coli* Cytosine Deaminase Gene to Human Colon Carcinoma–Derived Tumors Induces Chemosensitivity to 5–Fluorocytosine", (1995) Human Gene Therapy 6, 1055–1063.
Zhang et al., "Treatment of a human breast cancer xenograft with an adenovirus vector containing an interferon gene results in rapid regression due to viral oncolysis and gene therapy", (1996) Proc. Natl. Acad. Sci. USA 93, 4513–4518.
Ko et al., "Molecular Therapy with Recombinant p53 Adenovirus in an Androgen–Independent, Metastatic Human Prostate Cancer Model", (1996) Human Gene Therapy 7, 1683–1691.
Bischoff et al., "An Adenovirus Mutant That Replicates Selectively in p53–Deficient Human Tumor Cells", (1996) Science 274, 373–376.
Ohwada et al., "Regional Delivery of an Adenovirus Vector Containing the *Escherichia coli* Cytosine Deaminase Gene to Provide Local Activation of 5–Fluorocytosine to Suppress the Growth of Colon Carcinoma Metastatic to Liver", (1996) Human Gene Therapy 7, 1567–1576.
Elshami et al., "Treatment of Pleural Mesothelioma in an Immunocompetent Rat Model Utilizing Adenoviral Transfer of the Herpes Simplex Virus Thymidine Kinase Gene", (1996) Human Gene Therapy 7, 141–148.
Eastham et al., "Prostate Cancer Gene Therapy: Herpes Simplex Virus Thymidine Kinase Gene Transduction Followed by Ganciclovir in Mouse and Human Prostate Cancer Models", (1996) Human Gene Therapy 7, 515–523.

(List continued on next page.)

*Primary Examiner*—James Ketter
*Assistant Examiner*—Irem Yucel
*Attorney, Agent, or Firm*—Biogen, Inc.; Warren A. Kaplan

[57] ABSTRACT

The present invention relates to uses of mutant proto-oncogenes and oncoproteins expressed by the proto-oncogenes in inhibiting tumor growth and/or inhibiting the transformed phenotype. The preferred oncoprotein is a dominant, interfering mutant of a nuclear E2F transcription factor protein and is preferably a mutant E2F1 transcription factor protein. Methods of treating a target cell are described. Treatment is accomplished by administering to a target cell a dominant interfering mutant of a proto-oncogene in an effective amount. Treatment is also accomplished by administering to a target cell an oncoprotein in an effective amount. Compositions for such use are described as well.

23 Claims, 2 Drawing Sheets

OTHER PUBLICATIONS

Bramson et al., "Direct Intratumoral Injection of an Adenovirus Expressing Interleukin–12 Induces Regression and Long–Lasting Immunity That Is Associated with Highly Localized Expression of Interleukin–12", (1996) Human Gene Therapy 7, 1995–2002.

Riley et al., "Adenovirus–mediated retinoblastoma gene therapy suppresses spontaneous pituitary melanotroph tumors in Rb$^{+/-}$mice", (1996) Nature Medicine 2, 1316–1321.

Roth et al., "Retrovirus–mediated wild–type p53 gene transfer to tumors of patients with lung cancer", (1996) Nature Medicine 2, 985–991.

Xiaolan Qian, William C. Dougall, Maria E. Hellman & Mark I. Greene, "Kinase–deficient neu proteins suppress epidermal growth factor receptor function and abolish cell transformation", Oncogene 9(5) (1994), pp. 1507–1514.

Neyns, B. Teugels, E., Bourgain, C., Lissens, W., De Sutter, P., Burrer, M., De Greve, J., "Experimental Therapeutics", Proceedings of the American Association for Cancer Research, (Mar. 1995), vol. 36, p. 433.

Wilhelm Krek, David M. Livingston, Suman Shirodkar, "Binding to DNA and the Retinoblastoma Gene Product Promoted by Complex Formation of Different E2F Family Members", Science, (3 Dec. 1993), vol. 262, pp. 1557–1560.

Brown et al. Molecular and Cellular Biology, vol. 13 (11): 6849–6857, 1993.

Oliner et al. Nature, vol. 362, pp. 857–860, 1993.

Leng et al. Oncogene, vol. 10(7): 1275–82 Apr. 6, 1995.

Ali et al., The use of DNA viruses as vectors for gene therapy, *Gene Therapy* 1:367–384 (1994).

Helin et al., A cDNA encoding a pRB–binding protein with propertis of the transcription factor E2F, *Cell*, 70, 337–350 (1992).

Hijmans et al., E2F–5, a new E2F family member that interacts with p130 in vivo *Mollecular and Celleular Biology*, 15, 3082–3089 (1995).

Hoyle et al., Cloning and characterization of E2F–2, a novel protein with the biochemical properties of transcription factor E2F, *Molecular and Cellular Biology*, 13, 7802–7812 (1993).

Johnson et al., Oncogenic activity of the E2F1 gene, *Proc. Natl. Acad. Sci. USA*, 91, 12823–12827 (1994).

Kaelin et al., Expression cloning of a cDNA encoding a retinoblastoma–binding protein with E2F–like properties, *Cell*, 70, 351–364 (1992).

Kovesdi et al., Identification of a cellular transcription factor involved in E1A trans–action, *Cell*, 45, 219–228 (1986).

Lees et al., The retinoblastoma protein binds to a family of E2F transcription factors, *Molecular and Cellular Biology*, 13, 7813–7825 (1993).

Mulligan, The basic science of gene therapy, *Science*, 260, 926–932 (1993).

Nabel et al., Direct gene transfer with DNA–liposome complexes in melanoma: expression, biologic activity, and lack of toxicity in humans, *Proc. Natl. Acad. Sci. USA*, 90, 11307–11311 (1993).

Sardet et al., E2F–4 and E2F–5, two members of the E2F family, are expressed in the early phases of the cell cycle, *Proc. Natl. Acad. Sci. USA*, 92, 2403–2407 (1995).

Singh et al., Overexpression of E2F–1 in rat embryo fibroblasts leads to neoplastic transformation, *The EMBO Journal*, 13, 3329–3338 (1994).

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 2517 base pairs
( B ) TYPE: nucleic acid
( C ) STRANDEDNESS: double
( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
( A ) ORGANISM: Homo sapiens
( D ) DEVELOPMENTAL STAGE: Fetus
( F ) TISSUE TYPE: Brain
( G ) CELL TYPE: B-cell precursor
( H ) CELL LINE: Nalm 6

( i x ) FEATURE:
( A ) NAME/KEY: mat_peptide
( B ) LOCATION: 136..1446
( D ) OTHER INFORMATION: /function="pRB binding protein"
/ product= "E2F-1"

( x i ) SEQUENCE DESCRIPTION: SEQ ID NO:1:

| | | | | | | |
|---|---|---|---|---|---|---|
| GGAATTCCGT | GGCCGGGACT | TTGCAGGCAG | CGGCGGCCGG | GGGCGGAGCG | GGATCGAGCC | 6 0 |
| CTCGCCGAGG | CCTGCCGCCA | TGGGCCCGCG | CCGCCGCCGC | CGCCTGTCAC | CCGGGCCGCG | 1 2 0 |
| CGGGCCGTGA | GCGTCATGGC | CTTGGCCGGG | GCCCCTGCGG | GCGGCCCATG | CGCGCCGGCG | 1 8 0 |
| CTGGAGGCCC | TGCTCGGGGC | CGGCGCGCTG | CGGCTGCTCG | ACTCCTCGCA | GATCGTCATC | 2 4 0 |
| ATCTCCGCCG | CGCAGGACGC | CAGCGCCCCG | CCGGCTCCCA | CCGGCCCCGC | GGCGCCCGCC | 3 0 0 |
| GCCGGCCCCT | GCGACCCTGA | CCTGCTGCTC | TTCGCCACAC | CGCAGGCGCC | CCGGCCCACA | 3 6 0 |
| CCCAGTGCGC | CGCGGCCCGC | GCTCGGCCGC | CCGCCGGTGA | AGCGGAGGCT | GGACCTGGAA | 4 2 0 |
| ACTGACCATC | AGTACCTGGC | CGAGAGCAGT | GGGCCAGCTC | GGGGCAGAGG | CCGCCATCCA | 4 8 0 |
| GGAAAAGGTG | TGAAATCCCC | GGGGGAGAAG | TCACGCTATG | AGACCTCACT | GAATCTGACC | 5 4 0 |
| ACCAAGCGCT | TCCTGGAGCT | GCTGAGCCAC | TCGGCTGACG | GTGTCGTCGA | CCTGAACTGG | 6 0 0 |
| GCTGCCGAGG | TGCTGAAGGT | GCAGAAGCGG | CGCATCTATG | ACATCACCAA | CGTCCTTGAG | 6 6 0 |
| GGCATCCAGC | TCATTGCCAA | GAAGTCCAAG | AACCACATCC | AGTGGCTGGG | CAGCCACACC | 7 2 0 |
| ACAGTGGGCG | TCGGCGGACG | GCTTGAGGGG | TTGACCCAGG | ACCTCCGACA | GCTGCAGGAG | 7 8 0 |
| AGCGAGCAGC | AGCTGGACCA | CCTGATGAAT | ATCTGTACTA | CGCAGCTGCG | CCTGCTCTCC | 8 4 0 |
| GAGGACACTG | ACAGCCAGCG | CCTGGCCTAC | GTGACGTGTC | AGGACCTTCG | TAGCATTGCA | 9 0 0 |
| GACCCTGCAG | AGCAGATGGT | TATGGTGATC | AAAGCCCCTC | CTGAGACCCA | GCTCCAAGCC | 9 6 0 |
| GTGGACTCTT | CGGAGAACTT | TCAGATCTCC | CTTAAGAGCA | AACAAGGCCC | GATCGATGTT | 1 0 2 0 |
| TTCCTGTGCC | CTGAGGAGAC | CGTAGGTGGG | ATCAGCCCTG | GAAGACCCC | ATCCCAGGAG | 1 0 8 0 |
| GTCACTTCTG | AGGAGGAGAA | CAGGGCCACT | GACTCTGCCA | CCATAGTGTC | ACCACCACCA | 1 1 4 0 |
| TCATCTCCCC | CCTCATCCCT | CACCACAGAT | CCCAGCCAGT | CTCTACTCAG | CCTGGAGCAA | 1 2 0 0 |
| GAACCGCTGT | TGTCCCGGAT | GGGCAGCCTG | CGGGCTCCCG | TGGACGAGGA | CCGCCTGTCC | 1 2 6 0 |
| CCGCTGGTGG | CGGCCGACTC | GCTCCTGGAG | CATGTGCGGG | AGGACTTCTC | CGGCCTCCTC | 1 3 2 0 |

| | | | | | |
|---|---|---|---|---|---|
| CCTGAGGAGT | TCATCAGCCT | TTCCCCACCC | CACGAGGCCC | TCGACTACCA | CTTCGGCCTC | 1380 |
| GAGGAGGGCG | AGGGCATCAG | AGACCTCTTC | GACTGTGACT | TTGGGGACCT | CACCCCCCTG | 1440 |
| GATTTCTGAC | AGGGCTTGGA | GGGACCAGGG | TTTCCAGAGT | AGCTCACCTT | GTCTCTGCAG | 1500 |
| CCCTGGAGCC | CCCTGTCCCT | GGCCGTCCTC | CCAGCCTGTT | TGGAAACATT | TAATTTATAC | 1560 |
| CCCTCTCCTC | TGTCTCCAGA | AGCTTCTAGC | TCTGGGGTCT | GGCTACCGCT | AGGAGGCTGA | 1620 |
| GCAAGCCAGG | AAGGGAAGGA | GTCTGTGTGG | TGTGTATGTG | CATGCAGCCT | ACACCCACAC | 1680 |
| GTGTGTACCG | GGGGTGAATG | TGTGTGAGCA | TGTGTGTGTG | CATGTACCGG | GGAATGAAGG | 1740 |
| TGAACATACA | CCTCTGTGTG | TGCACTGCAG | ACACGCCCCA | GTGTGTCCAC | ATGTGTGTGC | 1800 |
| ATGAGTCCAT | CTCTGCGCGT | GGGGGGGCTC | TAACTGCACT | TTCGGCCCTT | TTGCTCGTGG | 1860 |
| GGTCCCACAA | GGCCCAGGGC | AGTGCCTGCT | CCCAGAATCT | GGTGCTCTGA | CCAGGCCAGG | 1920 |
| TGGGGAGGCT | TTGGCTGGCT | GGGCGTGTAG | GACGGTGAGA | GCACTTCTGT | CTTAAAGGTT | 1980 |
| TTTTCTGATT | GAAGCTTTAA | TGGAGCGTTA | TTTATTTATC | GAGGCCTCTT | TGGTGAGCCT | 2040 |
| GGGGAATCAG | CAAAAGGGGA | GGAGGGGTGT | GGGGTTGATA | CCCCAACTCC | CTCTACCCTT | 2100 |
| GAGCAAGGGC | AGGGGTCCCT | GAGCTGTTCT | TCTGCCCCAT | ACTGAAGGAA | CTGAGGCCTG | 2160 |
| GGTGATTTAT | TTATTGGGAA | AGTGAGGGAG | GGAGACAGAC | TGACTGACAG | CCATGGGTGG | 2220 |
| TCAGATGGTG | GGGTGGGCCC | TCTCCAGGGG | GCCAGTTCAG | GGCCCAGCTG | CCCCCCAGGA | 2280 |
| TGGATATGAG | ATGGGAGAGG | TGAGTGGGGG | ACCTTCACTG | ATGTGGGCAG | GAGGGGTGGT | 2340 |
| GAAGGCCTCC | CCCAGCCCAG | ACCCTGTGGT | CCCTCCTGCA | GTGTCTGAAG | CGCCTGCCTC | 2400 |
| CCCACTGCTC | TGCCCCACCC | TCCAATCTGC | ACTTTGATTT | GCTTCCTAAC | AGCTCTGTTC | 2460 |
| CCTCCTGCTT | TGGTTTTAAT | AAATATTTTG | ATGACGTTAA | AAAAGGAAT | TCGATAT | 2517 |

(2) INFORMATION FOR SEQ ID NO:2:

(i) SEQUENCE CHARACTERISTICS:
        (A) LENGTH: 1766 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
        (A) ORGANISM: Homo sapiens
        (H) CELL LINE: HeLa (ix) FEATURE:
        (A) NAME/KEY: mat_peptide
        (B) LOCATION: 429..1739
        (D) OTHER INFORMATION: /product= "E2F-2"

(xi) SEQUENCE DESCRIPTION: SEQ ID NO:2:

| | | | | | |
|---|---|---|---|---|---|
| CAGGACTAGA | GAGCGAGCCG | CAAGGAAGTC | GGTGCAGTCG | AGACCCCCT | CCCCATCCCA | 60 |
| GCGCATCGCG | TCTCCGCCGA | GCTTGAGGGC | ACGCCGGGGA | CCCCTCCCCA | GAGCCGGCCG | 120 |
| GACCCCAGGT | GCCGAGGCCT | TGGGGAGCGC | GGGGCGTCCC | GGGTCGCGGT | GCCCTCGGGA | 180 |
| CGAGACAGCC | CCTGGCAGTG | CCACCACCGC | AGCCGCCGGG | CGATCTCCAA | GCGGCGATCT | 240 |
| CTAAGCGCTG | CTCTCTGCTC | GGCCGCGGGC | CAGGAGGGGA | GGGTCCGGCC | TTGCCCCGCA | 300 |
| GGCGTCCATT | GGCGGCTTCC | CCCGGCCTCC | GCGCCATGCC | GCGGGCCGTG | TGAAAGGCGG | 360 |
| CAGCACCGGA | ACCCGCAGGT | GTCCGCGGGC | GCGCCAAGCC | CTTTTGGGTA | GGGGCGCCT | 420 |

```
TACTCGCTAT    GCTGCAAGGG    CCCCGGGCCT    TGGCTTCGGC    CGCTGGGCAG    ACCCCGAAGG        480

TGGTGCCCGC    GATGAGCCCC    ACAGAGCTGT    GGCCATCCGG    CCTCAGCAGC    CCCCAGCTCT        540

GCCCAGCTAC    TGCTACCTAC    TACACACCGC    TGTACCCGCA    GACGGCGCCT    CCCGCAGCGG        600

CGCCAGGCAC    CTGCCTCGAC    GCCACTCCCC    ACGGACCCGA    GGGCCAAGTT    GTGCGATGCC        660

TGCCGGCAGG    CCGGCTGCCG    GCCAAAAGGA    AGCTGGATCT    GGAGGGGATT    GGGAGGCCCG        720

TCGTCCCTGA    GTTCCCAACC    CCCAAGGGGA    AGTGCATCAG    AGTGGATGGC    CTCCCCAGCC        780

CCAAAACCCC    CAAATCCCCC    GGGGAGAAGA    CTCGGTATGA    CACTTCGCTG    GGGCTGCTCA        840

CCAAGAAGTT    CATTTACCTC    CTGAGCGAGT    CAGAGGATGG    GGTCCTGGAC    CTGAACTGGG        900

CCGCTGAGGT    GCTGGACGTG    CAGAAGCGGC    GCATCTATGA    CATCACCAAC    GTGCTGGAAG        960

GCATCCAGCT    CATCCGCAAG    AAGGCCAAGA    ACAACATCCA    GTGGGTAGGC    AGGGGAATGT       1020

TTGAAGACCC    CACCAGACCT    GGGAAGCAGC    AACAGCTGGG    GCAGGAGCTG    AAGGAGCTGA       1080

TGAACACGGA    GCAGGCCTTG    GACCAGCTCA    TCCAGAGCTG    CTCTCTGAGC    TTCAAGCACC       1140

TGACTGAGGA    CAAGGCCAAC    AAGAGGCTGG    CCTATGTGAC    TTACCAGGAT    ATCCGTGCTG       1200

TTGGCAACTT    TAAGGAGCAG    ACAGTGATTG    CCGTCAAGGC    CCCTCCGCAG    ACGAGACTGG       1260

AAGTGCCCGA    CAGGACTGAG    GACAACCTGC    AGATATATCT    CAAGAGCACC    CAAGGGCCCA       1320

TCGAAGTCTA    CCTGTGCCCA    GAGGAGGTGC    AGGAGCCGGA    CAGTCCTTCC    GAGGAGCCTC       1380

TCCCTCTAC    CTCCACCCTC    TGCCCCAGCC    CTGACTCTGC    CCAGCCAGC    AGCAGCACCG       1440

ACCCTAGCAT    CATGGAGCCC    ACAGCATCCT    CAGTGCCAGC    ACCAGCGCCA    ACCCCCCAGC       1500

AGGCCCCACC    GCCTCCATCC    CTGGTCCCCT    TGGAGGCTAC    TGACAGCCTG    CTGGAGCTGC       1560

CGCACCCACT    CCTGCAGCAG    ACTGAGGACC    AGTTCCTGTC    CCCGACCCTG    GCGTGCAGCT       1620

CCCCTCTGAT    CAGCTTCTCC    CCATCCTTGG    ACCAGGACGA    CTACCTGTGG    GGCTTGGAGG       1680

CGGGTGAGGG    CATCAGCGAT    CTCTTCGACT    CCTACGACCT    TGGGGACCTG    TTGATTAATT       1740

GAGTGGCCCT    GCCTGCCCCC    AGCAGC                                                    1766
```

( 2 ) INFORMATION FOR SEQ ID NO:3:

( i ) SEQUENCE CHARACTERISTICS:
            ( A ) LENGTH: 1332 base pairs
            ( B ) TYPE: nucleic acid
            ( C ) STRANDEDNESS: double
            ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
            ( A ) ORGANISM: Homo sapiens ( i x ) FEATURE:
            ( A ) NAME/KEY: mat_peptide
            ( B ) LOCATION: 63..1301
            ( D ) OTHER INFORMATION: /function="transcription factor"
                / product= "E2F-4"

( x i ) SEQUENCE DESCRIPTION: SEQ ID NO:3:

```
GCGCGGAAGT    GGCGCGGCGC    GCCTGGCCTG    GCCTGGCTGA    GGGGAGGCGG    CGGGCGGGCG         60

CGATGGCGGA    GGCCGGGCCA    CAGGCGCCGC    CGCCCCGGG    CACTCCAAGC    CGGCACGAAA        120

AGAGCCTGGG    ACTGCTCACC    ACCAAGTTCG    TGTCCCTTCT    GCAGGAGGCC    AAGGACGGCG        180

TGCTTGACCT    CAAGCTGGCA    GCTGACACCC    TAGCTGTACG    CCAGAAGCGG    CGGATTTACG        240
```

| | | | | | |
|---|---|---|---|---|---|
| ACATTACCAA | TGTTTTGGAA | GGTATCGGGC | TAATCGAGAA | AAAGTCCAAG | AACAGCATCC | 300 |
| AGTGGAAGGG | TGTGGGGCCT | GGCTGCAATA | CCCGGGAGAT | TGCTGACAAA | CTGATTGAGC | 360 |
| TCAAGGCAGA | GATCGAGGAG | CTGCAGCAGC | GGGAGCAAGA | ACTAGACCAG | CACAAGGTGT | 420 |
| GGGTGCAGCA | GAGCATCCGG | AACGTCACAG | AGGACGTGCA | GAACAGCTGT | TTGGCCTACG | 480 |
| TCACTCATGA | GGACATCTGC | AGATGCTTTG | CTGGAGATAC | CCTCTTGGCC | ATCCGGGCCC | 540 |
| CATCAGGCAC | CAGCCTGGAG | GTGCCCATCC | CAGAGGGTCT | CAATGGGCAG | AAGAAGTACC | 600 |
| AGATTCACCT | GAAGAGTGTG | AGTGGTCCCA | TTGAGGTTCT | GCTGGTGAAC | AAGGAGGCAT | 660 |
| GGAGCTCACC | CCCTGTGGCT | GTGCCTGTGC | CACCACCTGA | AGATTTGCTC | CAGAGCCAT | 720 |
| CTGCTGTTTC | TACACCTCCA | CCTCTGCCCA | AGCCTGCCCT | AGCCCAGTCC | CAGGAAGCCT | 780 |
| CACGTCCAAA | TAGTCCTCAG | CTCACTCCCA | CTGCTGTCCC | TGGCAGTGCA | GAAGTCCAGG | 840 |
| GAATGGCTGG | CCCAGCAGCT | GAGATCACAG | TGAGTGGCGG | CCCTGGGACT | GATAGCAAGG | 900 |
| ACAGTGGTGA | GCTCAGTTCA | CTCCCACTGG | GCCCAACAAC | ACTGGACACC | CGGCCACTGC | 960 |
| AGTCTTCTGC | CCTGCTGGAC | AGCAGCAGCA | GCAGCAGCAG | CAGCAGCAGC | AGCAGCAGCA | 1020 |
| ACAGTAACAG | CAGCAGTTCG | TCCGGACCCA | ACCCTTCTAC | CTCCTTTGAG | CCCATCAAGG | 1080 |
| CAGACCCCAC | AGGTGTTTTG | GAACTCCCCA | AAGAGCTGTC | AGAAATCTTT | GATCCACAC | 1140 |
| GAGAGTGCAT | GAGCTCGGAG | CTGCTGGAGG | AGTTGATGTC | CTCAGAAGTG | TTTGCCCCTC | 1200 |
| TGCTTCGTCT | TTCTCCACCC | CCGGGAGACC | ACGATTATAT | CTACAACCTG | GACGAGAGTG | 1260 |
| AAGGTGTCTG | TGACCTCTTT | GATGTGCCTG | TTCTCAACCT | CTGACTGACA | GGGACATGCC | 1320 |
| CTGTGTGGCT | GG | | | | | 1332 |

( 2 ) INFORMATION FOR SEQ ID NO:4:

( i ) SEQUENCE CHARACTERISTICS:
        ( A ) LENGTH: 591 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: mat_peptide
        ( B ) LOCATION: 1..588
        ( D ) OTHER INFORMATION: /product= "mutant E2F1a"

( x i ) SEQUENCE DESCRIPTION: SEQ ID NO:4:

| | | | | | |
|---|---|---|---|---|---|
| ATGGCCTTGG | CCGGGGCCCC | TGCGGGCGGC | CCATGCGCGC | CGGCGCTGGA | GGCCCTGCTC | 60 |
| GGGGCCGGCG | CGCTGCGGCT | GCTCGACTCC | TCGCAGATCG | TCATCATCTC | CGCCGCGCAG | 120 |
| GACGCCAGCG | CCCCGCCGGC | TCCCACCGGC | CCGCGGCGC | CCGCCGCCGG | CCCCTGCGAC | 180 |
| CCTGACCTGC | TGCTCTTCGC | CACACCGCAG | GCGCCCCGGC | CCACACCCAG | TGCGCCGCGG | 240 |
| CCCGCGCTCG | GCCGCCCGCC | GGTGAAGCGG | AGGCTGGACC | TGGAAACTGA | CCATCAGTAC | 300 |
| CTGGCCGAGA | GCAGTGGGCC | AGCTCGGGGC | AGAGGCCGCC | ATCCAGGAAA | AGGTGTGAAA | 360 |
| TCCCCGGGGG | AGAAGTCACG | CTATGAGACC | TCACTGAATC | TGACCACCAA | GCGCTTCCTG | 420 |
| GAGCTGCTGA | GCCACTCGGC | TGACGGTGTC | GTCGACCTGA | ACTGGGCTGC | CGAGGTGCTG | 480 |
| AAGGTGCAGA | AGCGGCGCAT | CTATGACATC | ACCAACGTCC | TTGAGGGCAT | CCAGCTCATT | 540 |
| GCCAAGAAGT | CCAAGAACCA | CATCCAGTGG | CTGGGCAGCC | ACACCACATG | A | 591 |

( 2 ) INFORMATION FOR SEQ ID NO:5:

( i ) SEQUENCE CHARACTERISTICS:
        ( A ) LENGTH: 1100 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: mat_peptide
        ( B ) LOCATION: 1..1098
        ( D ) OTHER INFORMATION: /product= "E2F1b mutant"

( x i ) SEQUENCE DESCRIPTION: SEQ ID NO:5:

```
ATGGCCTTGG  CCGGGGCCCC  TGCGGGCGGC  CCATGCGCGC  CGGCGCTGGA  GGCCCTGCTC       60
GGGGCCGGCG  CGCTGCGGCT  GCTCGACTCC  TCGCAGATCG  TCATCATCTC  CGCCGCGCAG      120
GACGCCAGCG  CCCCGCCGGC  TCCCACCGGC  CCCGCGGCGC  CCGCCGCCGG  CCCCTGCGAC      180
CCTGACCTGC  TGCTCTTCGC  CACACCGCAG  GCGCCCCGGC  CCACACCCAG  TGCGCCGCGG      240
CCCGCGCTCG  GCCGCCCGCC  GGTGAAGCGG  AGGCTGGACC  TGGAAACTGA  CCATCAGTAC      300
CTGGCCGAGA  GCAGTGGGCC  AGCTCGGGGC  AGAGGCCGCC  ATCCAGGAAA  AGGTGTGAAA      360
TCCCCGGGGG  AGAAGTCACG  CGCCAAGAAG  TCCAAGAACC  ACATCCAGTG  GCTGGGCAGC      420
CACACCACAG  TGGGCGTCGG  CGGACGGCTT  GAGGGGTTGA  CCCAGGACCT  CCGACAGCTG      480
CAGGAGAGCG  AGCAGCAGCT  GGACCACCTG  ATGAATATCT  GTACTACGCA  GCTGCGCCTG      540
CTCTCCGAGG  ACACTGACAG  CCAGCGCCTG  GCCTACGTGA  CGTGTCAGGA  CCTTCGTAGC      600
ATTGCAGACC  CTGCAGAGCA  GATGGTTATG  GTGATCAAAG  CCCCTCCTGA  GACCCAGCTC      660
CAAGCCGTGG  ACTCTTCGGA  GAACTTTCAG  ATCTCCCTTA  AGAGCAAACA  AGGCCCGATC      720
GATGTTTTCC  TGTGCCCTGA  GGAGACCGTA  GGTGGGATCA  GCCCTGGGAA  GACCCCATCC      780
CAGGAGGTCA  CTTCTGAGGA  GGAGAACAGG  GCCACTGACT  CTGCCACCAT  AGTGTCACCA      840
CCACCATCAT  CTCCCCCCTC  ATCCCTCACC  ACAGATCCCA  GCCAGTCTCT  ACTCAGCCTG      900
GAGCAAGAAC  CGCTGTTGTC  CCGGATGGGC  AGCCTGCGGG  CTCCCGTGGA  CGAGGACCGC      960
CTGTCCCCGC  TGGTGGCGGC  CGACTCGCTC  CTGGAGCATG  TGCGGGAGGA  CTTCTCCGGC     1020
CTCCTCCCTG  AGGAGTTCAT  CAGCCTTTCC  CCACCCCACG  AGGCCTGTGA  CTTTGGGGAC     1080
CTCACCCCCC  TGGATTTCTG                                                    1100
```

( 2 ) INFORMATION FOR SEQ ID NO:6:

( i ) SEQUENCE CHARACTERISTICS:
        ( A ) LENGTH: 437 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:6:

```
Met  Ala  Leu  Ala  Gly  Ala  Pro  Ala  Gly  Gly  Pro  Cys  Ala  Pro  Ala  Leu
 1              5                        10                        15
```

```
Glu  Ala  Leu  Leu  Gly  Ala  Gly  Ala  Leu  Arg  Leu  Leu  Asp  Ser  Ser  Gln
               20                      25                      30

Ile  Val  Ile  Ile  Ser  Ala  Ala  Gln  Asp  Ala  Ser  Ala  Pro  Pro  Ala  Pro
               35                      40                      45

Thr  Gly  Pro  Ala  Ala  Pro  Ala  Ala  Gly  Pro  Cys  Asp  Pro  Asp  Leu  Leu
      50                      55                      60

Leu  Phe  Ala  Thr  Pro  Gln  Ala  Pro  Arg  Pro  Thr  Pro  Ser  Ala  Pro  Arg
65                       70                      75                           80

Pro  Ala  Leu  Gly  Arg  Pro  Pro  Val  Lys  Arg  Arg  Leu  Asp  Leu  Glu  Thr
                    85                      90                      95

Asp  His  Gln  Tyr  Leu  Ala  Glu  Ser  Ser  Gly  Pro  Ala  Arg  Gly  Arg  Gly
                    100                     105                     110

Arg  His  Pro  Gly  Lys  Gly  Val  Lys  Ser  Pro  Gly  Glu  Lys  Ser  Arg  Tyr
               115                     120                     125

Glu  Thr  Ser  Leu  Asn  Leu  Thr  Thr  Lys  Arg  Phe  Leu  Glu  Leu  Leu  Ser
      130                     135                     140

His  Ser  Ala  Asp  Gly  Val  Val  Asp  Leu  Asn  Trp  Ala  Ala  Glu  Val  Leu
145                      150                     155                          160

Lys  Val  Gln  Lys  Arg  Arg  Ile  Tyr  Asp  Ile  Thr  Asn  Val  Leu  Glu  Gly
                    165                     170                     175

Ile  Gln  Leu  Ile  Ala  Lys  Lys  Ser  Lys  Asn  His  Ile  Gln  Trp  Leu  Gly
               180                     185                     190

Ser  His  Thr  Thr  Val  Gly  Val  Gly  Gly  Arg  Leu  Glu  Gly  Leu  Thr  Gln
          195                     200                     205

Asp  Leu  Arg  Gln  Leu  Gln  Glu  Ser  Glu  Gln  Gln  Leu  Asp  His  Leu  Met
      210                     215                     220

Asn  Ile  Cys  Thr  Thr  Gln  Leu  Arg  Leu  Leu  Ser  Glu  Asp  Thr  Asp  Ser
225                      230                     235                          240

Gln  Arg  Leu  Ala  Tyr  Val  Thr  Cys  Gln  Asp  Leu  Arg  Ser  Ile  Ala  Asp
                    245                     250                     255

Pro  Ala  Glu  Gln  Met  Val  Met  Val  Ile  Lys  Ala  Pro  Pro  Glu  Thr  Gln
               260                     265                     270

Leu  Gln  Ala  Val  Asp  Ser  Ser  Glu  Asn  Phe  Gln  Ile  Ser  Leu  Lys  Ser
          275                     280                     285

Lys  Gln  Gly  Pro  Ile  Asp  Val  Phe  Leu  Cys  Pro  Glu  Glu  Thr  Val  Gly
     290                     295                     300

Gly  Ile  Ser  Pro  Gly  Lys  Thr  Pro  Ser  Gln  Glu  Val  Thr  Ser  Glu  Glu
305                      310                     315                          320

Glu  Asn  Arg  Ala  Thr  Asp  Ser  Ala  Thr  Ile  Val  Ser  Pro  Pro  Pro  Ser
                    325                     330                     335

Ser  Pro  Pro  Ser  Ser  Leu  Thr  Thr  Asp  Pro  Gln  Ser  Leu  Leu  Ser
               340                     345                     350

Leu  Glu  Gln  Glu  Pro  Leu  Leu  Ser  Arg  Met  Gly  Ser  Leu  Arg  Ala  Pro
          355                     360                     365

Val  Asp  Glu  Asp  Arg  Leu  Ser  Pro  Leu  Val  Ala  Ala  Asp  Ser  Leu  Leu
     370                     375                     380

Glu  His  Val  Arg  Glu  Asp  Phe  Ser  Gly  Leu  Leu  Pro  Glu  Glu  Phe  Ile
385                      390                     395                          400

Ser  Leu  Ser  Pro  Pro  His  Glu  Ala  Leu  Asp  Tyr  His  Phe  Gly  Leu  Glu
                    405                     410                     415

Glu  Gly  Glu  Gly  Ile  Arg  Asp  Leu  Phe  Asp  Cys  Asp  Phe  Gly  Asp  Leu
               420                     425                     430
```

Thr Pro Leu Asp Phe
         435

(2) INFORMATION FOR SEQ ID NO:7:

(i) SEQUENCE CHARACTERISTICS:
        (A) LENGTH: 437 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:7:

```
Met Leu Gln Gly Pro Arg Ala Leu Ala Ser Ala Ala Gly Gln Thr Pro
 1               5                  10                  15

Lys Val Val Pro Ala Met Ser Pro Thr Glu Leu Trp Pro Ser Gly Leu
             20                  25                  30

Ser Ser Pro Gln Leu Cys Pro Ala Thr Ala Thr Tyr Tyr Thr Pro Leu
         35                  40                  45

Tyr Pro Gln Thr Ala Pro Pro Ala Ala Ala Pro Gly Thr Cys Leu Asp
     50                  55                  60

Ala Thr Pro His Gly Pro Glu Gly Gln Val Val Arg Cys Leu Pro Ala
 65                  70                  75                  80

Gly Arg Leu Pro Ala Lys Arg Lys Leu Asp Leu Glu Gly Ile Gly Arg
                 85                  90                  95

Pro Val Val Pro Glu Phe Pro Thr Pro Lys Gly Lys Cys Ile Arg Val
            100                 105                 110

Asp Gly Leu Pro Ser Pro Lys Thr Pro Lys Ser Pro Gly Glu Lys Thr
            115                 120                 125

Arg Tyr Asp Thr Ser Leu Gly Leu Leu Thr Lys Lys Phe Ile Tyr Leu
    130                 135                 140

Leu Ser Glu Ser Glu Asp Gly Val Leu Asp Leu Asn Trp Ala Ala Glu
145                 150                 155                 160

Val Leu Asp Val Gln Lys Arg Arg Ile Tyr Asp Ile Thr Asn Val Leu
                165                 170                 175

Glu Gly Ile Gln Leu Ile Arg Lys Lys Ala Lys Asn Asn Ile Gln Trp
            180                 185                 190

Val Gly Arg Gly Met Phe Glu Asp Pro Thr Arg Pro Gly Lys Gln Gln
        195                 200                 205

Gln Leu Gly Gln Glu Leu Lys Glu Leu Met Asn Thr Glu Gln Ala Leu
    210                 215                 220

Asp Gln Leu Ile Gln Ser Cys Ser Leu Ser Phe Lys His Leu Thr Glu
225                 230                 235                 240

Asp Lys Ala Asn Lys Arg Leu Ala Tyr Val Thr Tyr Gln Asp Ile Arg
                245                 250                 255

Ala Val Gly Asn Phe Lys Glu Gln Thr Val Ile Ala Val Lys Ala Pro
            260                 265                 270

Pro Gln Thr Arg Leu Glu Val Pro Asp Arg Thr Glu Asp Asn Leu Gln
        275                 280                 285

Ile Tyr Leu Lys Ser Thr Gln Gly Pro Ile Glu Val Tyr Leu Cys Pro
    290                 295                 300

Glu Glu Val Gln Glu Pro Asp Ser Pro Ser Glu Pro Leu Pro Ser
305                 310                 315                 320
```

```
        Thr  Ser  Thr  Leu  Cys  Pro  Ser  Pro  Asp  Ser  Ala  Gln  Pro  Ser  Ser  Ser
                            325                      330                      335

Thr  Asp  Pro  Ser  Ile  Met  Glu  Pro  Thr  Ala  Ser  Ser  Val  Pro  Ala  Pro
                       340                      345                      350

Ala  Pro  Thr  Pro  Gln  Gln  Ala  Pro  Pro  Pro  Ser  Leu  Val  Pro  Leu
                  355                      360                      365

Glu  Ala  Thr  Asp  Ser  Leu  Leu  Glu  Leu  Pro  His  Pro  Leu  Leu  Gln  Gln
             370                      375                      380

Thr  Glu  Asp  Gln  Phe  Leu  Ser  Pro  Thr  Leu  Ala  Cys  Ser  Ser  Pro  Leu
        385                      390                      395                           400

Ile  Ser  Phe  Ser  Pro  Ser  Leu  Asp  Gln  Asp  Asp  Tyr  Leu  Trp  Gly  Leu
                            405                      410                      415

Glu  Ala  Gly  Glu  Gly  Ile  Ser  Asp  Leu  Phe  Asp  Ser  Tyr  Asp  Leu  Gly
                       420                      425                      430

Asp  Leu  Leu  Ile  Asn
                  435
```

( 2 ) INFORMATION FOR SEQ ID NO:8:

( i ) SEQUENCE CHARACTERISTICS:
        ( A ) LENGTH: 413 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:8:

```
        Met  Ala  Glu  Ala  Gly  Pro  Gln  Ala  Pro  Pro  Pro  Gly  Thr  Pro  Ser
        1                   5                        10                      15

Arg  His  Glu  Lys  Ser  Leu  Gly  Leu  Leu  Thr  Thr  Lys  Phe  Val  Ser  Leu
                       20                      25                       30

Leu  Gln  Glu  Ala  Lys  Asp  Gly  Val  Leu  Asp  Leu  Lys  Leu  Ala  Ala  Asp
                  35                       40                      45

Thr  Leu  Ala  Val  Arg  Gln  Lys  Arg  Arg  Ile  Tyr  Asp  Ile  Thr  Asn  Val
             50                       55                      60

Leu  Glu  Gly  Ile  Gly  Leu  Ile  Glu  Lys  Lys  Ser  Lys  Asn  Ser  Ile  Gln
        65                       70                      75                           80

Trp  Lys  Gly  Val  Gly  Pro  Gly  Cys  Asn  Thr  Arg  Glu  Ile  Ala  Asp  Lys
                            85                      90                       95

Leu  Ile  Glu  Leu  Lys  Ala  Glu  Ile  Glu  Glu  Leu  Gln  Gln  Arg  Glu  Gln
                       100                      105                      110

Glu  Leu  Asp  Gln  His  Lys  Val  Trp  Val  Gln  Gln  Ser  Ile  Arg  Asn  Val
                  115                      120                      125

Thr  Glu  Asp  Val  Gln  Asn  Ser  Cys  Leu  Ala  Tyr  Val  Thr  His  Glu  Asp
             130                      135                      140

Ile  Cys  Arg  Cys  Phe  Ala  Gly  Asp  Thr  Leu  Leu  Ala  Ile  Arg  Ala  Pro
        145                      150                      155                           160

Ser  Gly  Thr  Ser  Leu  Glu  Val  Pro  Ile  Pro  Glu  Gly  Leu  Asn  Gly  Gln
                            165                      170                      175

Lys  Lys  Tyr  Gln  Ile  His  Leu  Lys  Ser  Val  Ser  Gly  Pro  Ile  Glu  Val
                       180                      185                      190

Leu  Leu  Val  Asn  Lys  Glu  Ala  Trp  Ser  Ser  Pro  Pro  Val  Ala  Val  Pro
                  195                      200                      205
```

-continued

| | | | | | | | | | | | | | | |
|---|---|---|---|---|---|---|---|---|---|---|---|---|---|---|
|Val|Pro 210|Pro|Pro|Glu|Asp 215|Leu|Leu|Gln|Ser|Pro 220|Ser|Ala|Val|Ser|Thr|
|Pro 225|Pro|Pro|Leu|Pro|Lys 230|Pro|Ala|Leu|Ala|Gln 235|Ser|Gln|Glu|Ala|Ser 240|
|Arg|Pro|Asn|Ser|Pro 245|Gln|Leu|Thr|Pro|Thr 250|Ala|Val|Pro|Gly|Ser 255|Ala|
|Glu|Val|Gln|Gly 260|Met|Ala|Gly|Pro|Ala 265|Ala|Glu|Ile|Thr|Val 270|Ser|Gly|
|Gly|Pro|Gly 275|Thr|Asp|Ser|Lys|Asp 280|Ser|Gly|Glu|Leu|Ser 285|Ser|Leu|Pro|
|Leu|Gly 290|Pro|Thr|Thr|Leu|Asp 295|Thr|Arg|Pro|Leu|Gln 300|Ser|Ser|Ala|Leu|
|Leu 305|Asp|Ser|Ser|Ser|Ser 310|Ser|Ser|Ser|Ser|Ser 315|Ser|Ser|Ser|Ser|Asn 320|
|Ser|Asn|Ser|Ser|Ser 325|Ser|Ser|Gly|Pro|Asn 330|Pro|Ser|Thr|Ser|Phe 335|Glu|
|Pro|Ile|Lys|Ala 340|Asp|Pro|Thr|Gly|Val 345|Leu|Glu|Leu|Pro|Lys 350|Glu|Leu|
|Ser|Glu|Ile 355|Phe|Asp|Pro|Thr|Arg 360|Glu|Cys|Met|Ser|Ser 365|Glu|Leu|Leu|
|Glu|Glu 370|Leu|Met|Ser|Ser|Glu 375|Val|Phe|Ala|Pro|Leu 380|Leu|Arg|Leu|Ser|
|Pro 385|Pro|Pro|Gly|Asp|His 390|Asp|Tyr|Ile|Tyr|Asn 395|Leu|Asp|Glu|Ser|Glu 400|
|Gly|Val|Cys|Asp|Leu 405|Phe|Asp|Val|Pro|Val 410|Leu|Asn|Leu| | | |

( 2 ) INFORMATION FOR SEQ ID NO:9:

( i ) SEQUENCE CHARACTERISTICS:
        ( A ) LENGTH: 196 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( x i ) SEQUENCE DESCRIPTION: SEQ ID NO:9:

| | | | | | | | | | | | | | | |
|---|---|---|---|---|---|---|---|---|---|---|---|---|---|---|
|Met 1|Ala|Leu|Ala|Gly 5|Ala|Pro|Ala|Gly|Gly 10|Pro|Cys|Ala|Pro|Ala 15|Leu|
|Glu|Ala|Leu|Leu 20|Gly|Ala|Gly|Ala|Leu 25|Arg|Leu|Leu|Asp|Ser 30|Ser|Gln|
|Ile|Val|Ile 35|Ile|Ser|Ala|Ala|Gln 40|Asp|Ala|Ser|Ala|Pro 45|Pro|Ala|Pro|
|Thr|Gly 50|Pro|Ala|Ala|Pro|Ala 55|Ala|Gly|Pro|Cys|Asp 60|Pro|Asp|Leu|Leu|
|Leu 65|Phe|Ala|Thr|Pro|Gln 70|Ala|Pro|Arg|Pro|Thr 75|Pro|Ser|Ala|Pro|Arg 80|
|Pro|Ala|Leu|Gly|Arg 85|Pro|Pro|Val|Lys|Arg 90|Arg|Leu|Asp|Leu|Glu 95|Thr|
|Asp|His|Gln|Tyr|Leu 100|Ala|Glu|Ser|Ser|Gly 105|Pro|Ala|Arg|Gly|Arg 110|Gly|
|Arg|His|Pro|Gly 115|Lys|Gly|Val|Lys|Ser 120|Pro|Gly|Glu|Lys|Ser 125|Arg|Tyr|

```
Glu  Thr  Ser  Leu  Asn  Leu  Thr  Thr  Lys  Arg  Phe  Leu  Glu  Leu  Leu  Ser
     130                      135                      140

His  Ser  Ala  Asp  Gly  Val  Val  Asp  Leu  Asn  Trp  Ala  Ala  Glu  Val  Leu
145                      150                      155                       160

Lys  Val  Gln  Lys  Arg  Arg  Ile  Tyr  Asp  Ile  Thr  Asn  Val  Leu  Glu  Gly
                    165                      170                      175

Ile  Gln  Leu  Ile  Ala  Lys  Lys  Ser  Lys  Asn  His  Ile  Gln  Trp  Leu  Gly
               180                      185                      190

Ser  His  Thr  Thr
          195
```

(2) INFORMATION FOR SEQ ID NO:10:

(i) SEQUENCE CHARACTERISTICS:
        (A) LENGTH: 365 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO:10:

```
Met  Ala  Leu  Ala  Gly  Ala  Pro  Ala  Gly  Gly  Pro  Cys  Ala  Pro  Ala  Leu
1                   5                   10                            15

Glu  Ala  Leu  Leu  Gly  Ala  Gly  Ala  Leu  Arg  Leu  Leu  Asp  Ser  Ser  Gln
               20                       25                      30

Ile  Val  Ile  Ile  Ser  Ala  Ala  Gln  Asp  Ala  Ser  Ala  Pro  Pro  Ala  Pro
          35                       40                      45

Thr  Gly  Pro  Ala  Ala  Pro  Ala  Ala  Gly  Pro  Cys  Asp  Pro  Asp  Leu  Leu
     50                       55                      60

Leu  Phe  Ala  Thr  Pro  Gln  Ala  Pro  Arg  Pro  Thr  Pro  Ser  Ala  Pro  Arg
65                       70                      75                       80

Pro  Ala  Leu  Gly  Arg  Pro  Pro  Val  Lys  Arg  Arg  Leu  Asp  Leu  Glu  Thr
                    85                       90                      95

Asp  His  Gln  Tyr  Leu  Ala  Glu  Ser  Ser  Gly  Pro  Ala  Arg  Gly  Arg  Gly
                    100                      105                     110

Arg  His  Pro  Gly  Lys  Gly  Val  Lys  Ser  Pro  Gly  Glu  Lys  Ser  Arg  Lys
          115                      120                     125

Lys  Ser  Lys  Asn  His  Ile  Gln  Trp  Leu  Gly  Ser  His  Thr  Thr  Val  Gly
     130                      135                      140

Val  Gly  Gly  Arg  Leu  Glu  Gly  Leu  Thr  Gln  Asp  Leu  Arg  Gln  Leu  Gln
145                      150                      155                      160

Glu  Ser  Glu  Gln  Gln  Leu  Asp  His  Leu  Met  Asn  Ile  Cys  Thr  Thr  Gln
                    165                      170                     175

Leu  Arg  Leu  Leu  Ser  Glu  Asp  Thr  Asp  Ser  Gln  Arg  Leu  Ala  Tyr  Val
               180                      185                     190

Thr  Cys  Gln  Asp  Leu  Arg  Ser  Ile  Ala  Asp  Pro  Ala  Glu  Gln  Met  Val
          195                      200                     205

Met  Val  Ile  Lys  Ala  Pro  Pro  Glu  Thr  Gln  Leu  Gln  Ala  Val  Asp  Ser
     210                      215                     220

Ser  Glu  Asn  Phe  Gln  Ile  Ser  Leu  Lys  Ser  Lys  Gln  Gly  Pro  Ile  Asp
225                      230                     235                      240

Val  Phe  Leu  Cys  Pro  Glu  Glu  Thr  Val  Gly  Gly  Ile  Ser  Pro  Gly  Lys
                    245                      250                     255
```

|     |     |     |     |     |     |     |     |     |     |     |     |     |     |     |
| --- | --- | --- | --- | --- | --- | --- | --- | --- | --- | --- | --- | --- | --- | --- |
| Thr | Pro | Ser | Gln<br>260 | Glu | Val | Thr | Ser | Glu<br>265 | Glu | Glu | Asn | Arg | Ala<br>270 | Thr | Asp |
| Ser | Ala | Thr<br>275 | Ile | Val | Ser | Pro | Pro<br>280 | Pro | Ser | Ser | Pro | Pro<br>285 | Ser | Ser | Leu |
| Thr | Thr<br>290 | Asp | Pro | Ser | Gln | Ser<br>295 | Leu | Leu | Ser | Leu | Glu<br>300 | Gln | Glu | Pro | Leu |
| Leu<br>305 | Ser | Arg | Met | Gly | Ser<br>310 | Leu | Arg | Ala | Pro | Val<br>315 | Asp | Glu | Asp | Arg | Leu<br>320 |
| Ser | Pro | Leu | Val | Ala<br>325 | Ala | Asp | Ser | Leu | Leu<br>330 | Glu | His | Val | Arg | Glu<br>335 | Asp |
| Phe | Ser | Gly | Leu<br>340 | Leu | Pro | Glu | Glu | Phe<br>345 | Ile | Ser | Leu | Ser | Pro<br>350 | Pro | His |
| Glu | Ala | Cys<br>355 | Asp | Phe | Gly | Asp | Leu<br>360 | Thr | Pro | Leu | Asp | Phe<br>365 |     |     |     |

(2) INFORMATION FOR SEQ ID NO:11:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "oligonucleotide"

(iii) HYPOTHETICAL: NO (iv) ANTI-SENSE: NO (xi) SEQUENCE DESCRIPTION: SEQ ID NO:11:

CCGGGGAGAA GTCACGCGCT AGCGCCAAGA AGTCCAAGAA C    41

(2) INFORMATION FOR SEQ ID NO:12:

(i) SEQUENCE CHARACTERISTICS:
(A) LENGTH: 42 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "oligonucleotide"

(iii) HYPOTHETICAL: NO (iv) ANTI-SENSE: NO (xi) SEQUENCE DESCRIPTION: SEQ ID NO:12:

TCCCCACCCC ACGAGGCCGC TAGCTGTGAC TTTGGGGACC TC    42

GENE THERAPY METHODS AND COMPOSITIONS

BACKGROUND OF THE INVENTION

The human genome possesses genes which have the potential, when mutated or expressed at higher than normal levels, to lead to the formation of cancer. The first genes to be identified which had this property were viral oncogenes. The products of these viral oncogenes are responsible for the virus' ability to form tumorigenic cells having altered growth properties. The corresponding cellular oncogenes ("proto-oncogenes") can be activated by viruses, chromosomal rearrangement, gene amplification or mutation.

In all, more than 25 distinct proto-oncogenes have been identified in mammalian cells. See Hunter, *Cell*, 64: 249–270 (1991). In their normal context, proto-oncogenes have important functions in control of cell growth; they encode growth factors or their receptors (e.g., c-erbB proto-oncogene), they act as intracellular signal transducers (e.g., c-src, c-ras proto-oncogenes), and they are transcription factors that control expression of cellular genes required for cell proliferation (e.g.,c-myc, c-fos, c-jun proto-oncogenes). Proto-oncogene expression is tightly regulated with regard to both the level of expression and the timing of expression during development and during the cell cycle. Activation of proto-oncogenes often occurs through deregulation of their expression.

The genome also expresses genes which block cancer formation. These "anti-oncogenes", also called tumor suppressors, are negative regulators of cell division. The mutation and/or loss of these genes can lead to deregulated cell proliferation and a dramatically increased incidence of cancers. In fact, the most commonly mutated genes in human cancers are tumor suppressors. Individuals heterozygous for germ-line mutations in tumor suppressors are strongly predisposed to one or more types of cancer. The loss or mutation of the normal tumor suppressor gene in these heterozygous individuals can lead to tumor formation.

The first tumor suppressor discovered was the retinoblastoma susceptibility gene (RB) which was identified from studies on sporadic and inherited retinoblastoma. All normal human cells carry one copy of the RB gene on each chromosome 13. Rarely, a mutational event destroys one of the pair, but the cells are still phenotypically normal (i.e., the mutation is "recessive") as the remaining normal RB gene acts to inhibit cellular proliferation and tumorigenic potential. If a mutation or loss of the remaining normal RB gene occurs in these heterozygous cells, a tumor will develop. Tumorigenesis requiring these two mutations is exceedingly rare and only single tumors will develop. Since one of the RB genes is already nonfunctional at birth in the inherited form, single mutations can result in an RB−/− genotype and the likelihood of formation of tumors is far greater.

Mutations in the RB gene have been associated definitively with the occurrence of retinoblastomas. RB deletion or mutation has also been observed in a variety of other human tumors. Most notable among these other cancers are osteosarcoma as well as bone and soft-tissue sarcomas. RB loss or mutation is also strongly implicated in small cell lung carcinoma and, to a lesser extent, other lung cancers and esophageal carcinoma. Functional loss of RB has also been associated with cancer of the bladder, prostate, breast and liver, as well as lymphomas and leukemias.

The RB tumor suppressor protein forms complexes with a variety of cellular proteins that play a role in transcriptional regulation, in particular, the E2F family of cellular transcription factors. See Kovesdi et al., *Cell*, 45: 219–228, 1986. It is now known that the RB protein associates with E2F, specifically in mid-late G1 and S phase during the cell cycle. E2F-binding sites have been known to exist in a number of growth-regulatory genes. In particular, a subset of these genes encodes products that play a role in DNA synthesis. RB appears to form a complex with E2F which represses transcription of E2F-responsive promoters, thus inhibiting growth. Promoters such as those directing expression of dihydrofolate reductase (DHFR), DNA polymerase alpha, cdc2, and thymidine kinase all contain E2F-binding sites. See, for instance, Means et al., *Mol. Cell. Biol.*, 12:1054–1063 (1992)and Pearson et al., *Mol. Cell. Biol.*, 11:2081–2095 (1991). Inactivation of RB genes may effectively eliminate transcriptional repression of important genes involved in DNA synthesis.

Moreover, at least one E2F member, E2F1, has been demonstrated to be a target of RB action and exhibits oncogenic properties when overexpressed in immortalized cell lines or, in conjunction with activated ras oncogene. See, for example, Singh et al., U *J.*, 13: 3329–3338, (1994) and Johnson et al., *Proc. Nat. Acad. Sci. USA* 91: 12823–12827 (1994). The possibility exists that, in the case of certain RB−/− tumors, inactivation of RB has led to deregulated E2F activity and/or increased level of E2F expression.

It is theoretically possible to treat human RB (−/−) cancers through re-introduction of a wild-type RB gene. The exogenously delivered tumor suppressor is likely to inhibit tumor proliferation. It is known that re-introduction of the RB tumor suppressor gene into RB-defective tumor cells inhibits the tumor cell growth and inhibits the neoplastic phenotype of the target cells. See, for example, Huang et al., *Science*, 242: 1563–1566 (1988) and Bookstein et al., *Science*, 247: 712–715 (1990).

Nevertheless, gene therapy using RB tumor suppressor genes is problematic. Since RB (−/−) tumor cells have already mutated the resident RB gene, it is possible that these cells lacking tumor suppressor gene function have already evolved a mechanism to mutate or destabilize wild-type RB genes and might certainly possess the mechanism to mutate or destabilize the introduced wild-type RB gene.

In particular, it has been shown that several cell lines from tumors that have had the RB gene re-introduced have become very tumorigenic and have formed large, progressively growing tumors when injected into mice. See Zhou et al., *Proc. Am. Assoc. Cancer Res.*, 34: 3214 (1993). This phenomenon is called tumor suppressor gene resistance and might be due to the fact that the tumor cells may have inherited or acquired the ability to mutate or destabilize wild-type RB. Alternately, or in addition, the tumor cells may be able to convert RB proteins to an inactive (i.e., phosphorylated) form that allows tumor growth to continue.

Overexpression of tumor suppressor RB genes is likely to be cytotoxic to both tumor cells and proliferating normal cells. Thus, this therapy may be no more effective than conventional chemotherapy, which indiscriminately kills normal and abnormal cells. Moreover, inhibition of tumorigenicity using this approach is often incomplete and a significant percentage of the RB-reconstituted tumor cells (retaining normal RB expression) still form malignant and invasive tumors in nude mouse tumorigenicity assays. See Xu et al., *Cancer Res.*, 51: 4481–4485 (1991); Banerjee et al., *Cancer Res.*, 52: 6297–6304 (1992).

Accordingly, there is a need in the art for a genetic therapy for tumor or cancer cells which can safely overcome these problems.

SUMMARY OF THE INVENTION

We have solved the problems associated with gene therapy using tumor suppressor genes by developing a method of inhibiting cell growth which involves introducing into a tumor cell a dominant interfering mutant of an endogenous proto-oncogene, preferably an endogenous nuclear proto-oncogene that functions in vivo as a transcription factor. The expressed, mutant gene product (i.e., a mutant "oncoprotein")is defective for transcriptional activation and inhibits growth of tumor cells. In particular, we have found that mutant forms of the proto-oncogene E2F1 transcription factor will actively inhibit growth of RB(−/−) tumor cells by interfering with their endogenous wild-type counterpart at either the level of protein-DNA binding or protein-protein interaction. It appears that mutant E2F1 proto-oncogenes, and their mutant E2F1 oncoprotein gene products, can block the growth-stimulatory action of E2F transcription factors in the complete absence of RB.

One aspect of the present invention is a method of inhibiting growth of a target cell. The method includes providing an isolated, mutant proto-oncogene polynucleotide sequence to the target cell in which the mutant polynucleotide sequence, upon expression, encodes for a mutant of an oncoprotein. The target cell is combined with the mutant proto-oncogene polynucleotide sequence for a time and under conditions sufficient for expression of the mutant oncoprotein in the target cell. The mutant oncoprotein is capable of inhibiting growth of the target cell.

It is preferred that the isolated, mutant proto-oncogene polynucleotide sequence, upon expression, encodes a dominant interfering mutant of a transcription factor oncoprotein. The mutant proto-oncogene may selected from the group consisting of a mutant E2F1 polynucleotide sequence (or other E2F family member), mutant myc polynucleotide sequence, mutant mdm2 polynucleotide sequence, mutant myb polynucleotide sequence, mutant fos polynucleotide sequence, mutant jun polynucleotide sequence, mutant erbA polynucleotide sequence, mutant N-myc polynucleotide sequence, and a mutant L-myc polynucleotide sequence. Most preferably, the mutant is a dominant interfering mutant of an E2F1 polynucleotide sequence. The target cell can be mammalian tumor cell and is preferably a mammalian tumor cell lacking a functioning retinoblastoma gene.

In a preferred embodiment, a method of inhibiting growth of a tumor cell includes providing to the tumor cell an isolated, mutant of an E2F polynucleotide sequence in which the mutant, upon expression, encodes for a dominant interfering mutant of an E2F transcription factor oncoprotein. Next, the cell is incubated in the presence of the mutant E2F polynucleotide sequence for a time and under conditions sufficient for expression of the mutant E2F transcription factor oncoprotein in the target cell. The mutant E2F transcription factor oncoprotein is in an amount sufficient to inhibit growth of the tumor cell. It is preferred that the mutant E2F polynucleotide sequence is selected from the group consisting of SEQ ID NOS.: 4–5; a polynucleotide sequence that hybridizes to any of the foregoing sequences under standard hybridization conditions and that encodes a mutant oncoprotein having the cell growth inhibition activity of a dominant interfering mutant of an E2F transcription factor; and a polynucleotide sequence that codes on expression for a protein encoded by any of the foregoing polynucleotide sequences.

Alternately, a method of inhibiting growth of a target cell may also include providing an isolated, dominant interfering mutant oncoprotein to the target cell and incubating the target cell in the presence of the mutant oncoprotein for a time and under conditions sufficient for the mutant oncoprotein to inhibit growth of the target cell. It is preferred that the mutant oncoprotein comprise a mutant transcription factor such as a mutant E2F transcription factor, a mutant myc transcription factor, a mutant mdm2 transcription factor, a mutant myb transcription factor, a mutant fos transcription factor, a mutant jun transcription factor, a mutant erbA transcription factor, a mutant N-myc transcription factor, and a mutant L-myc transcription factor. Most preferably, the mutant transcription factor is a mutant E2F1 transcription factor. More generally, the mutant oncoprotein transcription factor comprises a protein encoded by a polynucleotide sequence selected from the group consisting of SEQ ID NOS.: 4–5; a polynucleotide sequence that hybridizes to any of the foregoing sequences under standard hybridization conditions; and a polynucleotide sequence that codes on expression for a protein encoded by any of the foregoing polynucleotide sequences. The mutant transcription factor may be combined with a carrier moiety for directing transport of the mutant transcription factor oncoprotein into the target cell. The mutant oncoprotein transcription factor also may comprise a protein selected from the group consisting of SEQ ID NOS.: 9–10.

Another method of the invention is a method for treating abnormal cellular proliferation in a mammal. The method includes administering an effective dose of an expression vector comprising a isolated, mutant E2F polynucleotide. The mutant polynucleotide encodes, upon expression, a dominant interfering mutant E2F transcription factor. The vector is administered to a mammal having cells exhibiting abnormal cellular proliferation such that the expression vector is inserted into the cells. The cells are allowed to express the mutant E2F transcription factor in an amount effective to inhibit proliferation of the abnormal cells. The expression vector includes a polynucleotide sequence selected from the group consisting of SEQ ID NOS.: 4–5; a polynucleotide sequence that hybridizes to any of the foregoing sequences under standard hybridization conditions; and a polynucleotide sequence that codes on expression for a protein encoded by any of the foregoing polynucleotide sequences. The expression vector is selected from plasmid vectors and viral vectors (e.g., retroviral, adenoviral, herpesviral, adeno-associated viral and the like). Preferred target cells are those that lack functional tumor suppressor genes. Methods of the invention have particular use in inhibiting growth of tumor cells, particularly those tumor cells that lack a functioning retinoblastoma gene [RB (−/−) cells].

An ex vivo method of treating a target cell of a mammalian subject is also encompassed by the invention. The method includes removing a tissue sample from the mammalian subject and then contacting the target cell with an effective amount of a isolated, mutant of an E2F polynucleotide sequence. Next, one allows expression of a dominant interfering mutant E2F transcription factor from the mutant E2F polynucleotide sequence within the target cell under conditions sufficient for the transcription factor to inhibit growth of the target cell, restore normal functioning of untransformed cells (e.g., secretion of cytokines) and/or inhibit development of the transformed phenotype. The target cell is then returned to the mammal or to another mammal. This method is particularly useful in allowing the phenotypically normal target cells to secrete factors which will inhibit growth/activity of the surrounding transformed tumor cells.

Compositions of the invention include an isolated, mutant proto-oncogene and a pharmaceutically acceptable carrier.

The mutant proto-oncogene sequence is a mutant proto-oncogene polynucleotide sequence which, upon expression, encodes a dominant interfering mutant transcription factor oncoprotein capable of inhibiting growth of a tumor cell. The preferred dominant interfering mutant is a mutant E2F transcription factor oncoprotein, most preferably a dominant interfering mutant of an E2F1 transcription factor oncoprotein. The mutant proto-oncogene sequence comprises a polynucleotide sequence selected from the group consisting of SEQ ID NOS.: 4–5; a polynucleotide sequence that hybridizes to any of the foregoing sequences under standard hybridization conditions and that encodes a mutant oncoprotein having the cell growth inhibition activity of a dominant interfering mutant of an E2F transcription factor; and a polynucleotide sequence that codes on expression for a protein encoded by any of the foregoing polynucleotide sequences.

A further composition of the invention comprises an isolated, mutant oncoprotein in a pharmaceutically acceptable carrier, the mutant oncoprotein in an amount sufficient to inhibit growth of a target cell when the mutant oncoprotein is present in the target cell. It is preferred that the mutant oncoprotein is a mutant transcription factor oncoprotein and is most preferably a mutant E2F1 transcription factor oncoprotein. The mutant transcription factor oncoprotein may be encoded by a polynucleotide sequence selected from the group consisting of SEQ ID NOS.: 4–5; a polynucleotide sequence that hybridizes to any of the foregoing sequences under standard hybridization conditions; a polynucleotide sequence that codes on expression for a protein encoded by any of the foregoing polynucleotide sequences. In one embodiment, the carrier comprises an HIV-1 tat protein and the target cell is a tumor cell lacking a functioning retinoblastoma gene. In this embodiment, the mutant oncoprotein transcription factor may also comprise a protein encoded selected from the group consisting of SEQ ID NOS.: 9–10.

Another aspect of the invention is a virus such as a retrovirus, adenovirus or an adeno-associated virus containing an isolated polynucleotide sequence that encodes for a dominant interfering mutant of a cellular oncoprotein. The mutant oncoprotein is a transcriptional factor encoded by a polynucleotide that includes: SEQ ID NOS.: 4–5, a polynucleotide that hybridizes to SEQ ID NOS.: 4–5; and a polynucleotide that codes on expression for a protein encoded by any of the foregoing sequences. These compositions containing virus and polynucleotide/oncoprotein have use in gene therapy and in assay systems.

In yet another embodiment of the invention, a tumor cell is provided that contains an isolated, mutant proto-oncogene. The mutant proto-oncogene, upon expression, encodes a mutant oncoprotein transcription factor that inhibits growth of the tumor cell or inhibits the transformed phenotype. The cell may contain a mutant E2F proto-oncogene, wherein the mutant, upon expression, encodes for a dominant interfering mutant E2F transcription factor.

A tumor cell may also contain an isolated, dominant interfering mutant oncoprotein transcription factor, the mutant transcription factor capable of inhibiting growth of the tumor cell. It is preferred that the isolated, mutant oncoprotein transcription factor is a mutant E2F transcription factor. This cell and associated polynucleotide/ oncoprotein sequences have use in an assay system to screen for mutagenic compounds. A tumor cell containing a polynucleotide sequence of a mutant proto-oncogene that codes, on expression, for a dominant interfering mutant of an oncoprotein (e.g., a mutant E2F1 oncoprotein) is challenged with a material suspected of being mutagenic. The effect of the material on overcoming the growth inhibitive effects of the mutant proto-oncogene is measured using methods described herein.

Another aspect of the invention is a method for inhibiting growth of a target cell by providing to the target cell an isolated, mutant proto-oncogene. The mutant proto-oncogene, upon expression, encodes a mutant oncoprotein that is capable of inhibiting growth of the target cell. Next the target cell is challenged with an environmental insult, preferably selected from the group consisting of gamma and X-ray irradiation. This method is useful as an adjunct to conventional cancer therapy since introduction of mutant proto-onocogenes into tumor cells sensitizes the tumor cells to a subsequent environmental challenge.

The practice of the present invention will employ, unless otherwise indicated, conventional techniques of cell biology, cell culture, molecular biology, microbiology and recombinant DNA technology, which are within the skill of the art. Such techniques are explained fully in the literature. See, for example, *Molecular Cloning: A Laboratory Manual*, 2nd ed., (Sambrook et al., eds.), Cold Spring Harbor Laboratory Press, 1989; *DNA Cloning*, Volumes I and II (N. D. Glover, ed.,) 1985; *Nucleic Acid Hybridization* (Hames and Higgins, eds.,), 1984; *Culture of Animal Cells* (R. I. Freshney), Alan R. Liss, Inc. 1987; *Gene Transfer Vectors for Mammalian Cells* (Miller and Calos, eds.,) Cold Spring Harbor Laboratory, 1987.

Other features and advantages of the invention will be apparent from he following detailed description, and from the claims.

---

LIST OF THE SEQUENCES

Figure 1:
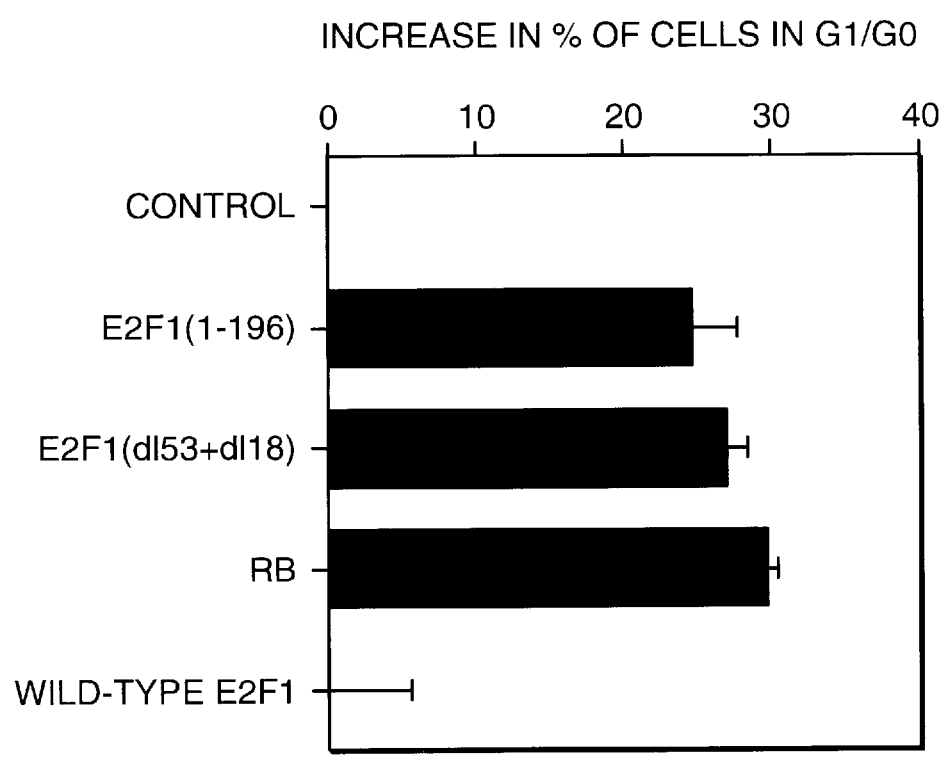
FIG. 1 is a bar graph plotting the percentage increase in cells that are in G1/G0 (relative to the control) as a function of the transfectant treatment.

SEQ ID NO.: 1 is a 2517 base pair complementary DNA
(cDNA) sequence encoding for wild-type E2F1 transcription.

```
  1 GGAATTCCGT GGCCGGGACT TTGCAGGCAG CGGCGGCCGG GGGCGGAGCG
 51 GGATCGAGCC CTCGCCGAGG CGTGCCGCCA TGGGCCCGCG CCGCCGCCGC
101 CGCCTGTCAC CCGGGCCGCG CGGGCCGTGA GCGTCATGGC CTTGGCCGGG
151 GCCCCTGCGG GCGGCCCATG CGCGCCGGCG CTGGAGGCCC TGCTCGGGGC
201 CGGCGCGCTG CGGCTGCTCG ACTCCTCGCA GATCGTCATC ATCTCCGCCG
```

| LIST OF THE SEQUENCES |
| --- |
| 251 CGCAGGACGC CAGCGCCCCG CCGGCTCCCA CCGGCCCCGC GGCGCCCGCC
301 GCCGGCCCCT GCGACCCTGA CCTGCTGCTC TTCGCCACAC CGCAGGCGCC
351 CCGGCCCACA CCCAGTGCGC CGCGGCCCGC GCTCGGCCGC CCGCCGGTGA
401 AGCGGAGGCT GGACCTGGAA ACTGACCATC AGTACCTGGC CGAGAGCAGT
451 GGGCCAGCTC GGGGCAGAGG CCGCCATCCA GGAAAAGGTG TGAAATCCCC
501 GGGGGAGAAG TCACGCTATG AGACCTCACT GAATCTGACC ACCAAGCGCT
551 TCCTGGAGCT GCTGAGCCAC TCGGCTGACG GTGTCGTCQA CCTGAACTGG
601 GCTGCCGAGG TGCTGAAGGT GCAGAAGCGG CGCATCTATG ACATCACCAA
651 CGTCCTTGAG GGCATCCAGC TCATTGCCAA GAAGTCCAAG AACCACATCC
701 AGTGGCTGGG CAGCCACACC ACAGTGGGCG TCGGCGGACG GCTTGAGGGG
751 TTGACCCAGG ACCTCCGACA GCTGCAGGAG AGCGAGCAGC AGCTGGACCA
801 CCTGATGAAT ATCTGTACTA CGCAGCTGCG CCTGCTCTCC GAGGACACTG
851 ACAGCCAGCG CCTGGCCTAC GTGACGTGTC AGGACCTTCG TAGCATTGCA
901 GACCCTGCAG AGCAGATGGT TATGGTGATC AAAGCCCCTC CTGAGACCCA
951 GCTCCAAGCC GTGGACTCTT CGGAGAACTT TCAGATCTCC CTTAAGAGCA
1001 AACAAGGCCC GATCGATGTT TTCCTGTGCC CTGAGGAGAC CGTAGGTGGG
1051 ATCAGCCCTG GGAAGACCCC ATCCCAGGAG GTCACTTCTG AGGAGGAGAA
1101 CAGGGCCACT GACTCTGCCA CCATAGTGTC ACCACCACCA TCATCTCCCC
1151 CCTCATCCCT CACCACAGAT CCCAGCCAGT CTCTACTCAG CCTGGAGCAA
1201 GAACCGCTGT TGTCCCGGAT GGGCAGCCTG CGGGCTCCCG TGGACGAGGA
1251 CCGCCTGTCC CCGCTGGTGG CGGCCGACTC GCTCCTGGAG CATGTGCGGG
1301 AGGACTTCTC CGGCCTCCTC CCTGAGGAGT TCATCAGCCT TTCCCCACCC
1351 CACGAGGCCC TCGACTACCA CTTCGGCCTC GAGGAGGGCG AGGGCATCAG
1401 AGACCTCTTC GACTGTGACT TGGGGACCT CACCCCCCTG GATTTCTGAC
1451 AGGGCTTGGA GGGACCAGGG TTTCCAGAGT AGCTCACCTT GTCTCTGCAG
1501 CCCTGGAGCC CCCTGTCCCT GGCCGTCCTC CCAGCCTGTT TGGAAACATT
1551 TAATTTATAC CCCTCTCCTC TGTCTCCAGA AGCTTCTAGC TCTGGGGTCT
1601 GGCTACCGCT AGGAGGCTGA GCAAGCCAGG AAGGGAAGGA GTCTGTGTGG
1651 TGTGTATGTG CATGCAGCCT ACACCCACAC GTGTGTACCG GGGGTGAATG
1701 TGTGTGAGCA TGTGTGTGTG CATGTACCGG GGAATGAAGG TGAACATACA
1751 CCTCTGTGTG TGCACTGCAG ACACGCCCCA GTGTGTCCAC ATGTGTGTGC
1801 ATGAGTCCAT CTCTGCGCGT GGGGGGGCTC TAACTGCACT TTCGGCCCTT
1851 TTGCTCGTGG GGTCCCACAA GGCCCAGGGC AGTGCCTGCT CCCAGAATCT
1901 GGTGCTCTGA CCAGGCCAGG TGGGGAGGCT TTGGCTGGCT GGGCGTGTAG
1951 GACGGTGAGA GCACTTCTGT CTTAAAGGTT TTTTCTGATT GAAGCTTTAA
2001 TGGAGCGTTA TTTATTTATC GAGGCCTCTT TGGTGAGCCT GGGGAATCAG
2051 CAAAAGGGGA GGAGGGGTGT GGGGTTGATA CCCCAACTCC CTCTACCCTT
2101 GAGCAAGGGC AGGGGTCCCT GAGCTGTTCT TCTGCCCCAT ACTGAAGGAA
2151 CTGAGGCCTG GGTGATTTAT TTATTGGGAA AGTGAGGGAG GGAGACAGAC
2201 TGACTGACAG CCATGGGTGG TCAGATGGTG GGGTGGGCCC TCTCCAGGGG
2251 GCCAGTTCAG GGCCCAGCTG CCCCCCAGGA TGGATATGAG ATGGGAGAGG
2301 TGAGTGGGGG ACCTTCACTG ATGTGGGCAG GAGGGGTGGT GAAGGCCTCC
2351 CCCAGCCCAG ACCCTGTGGT CCCTCCTGCA GTGTCTGAAG CGCCTGCCTC
2401 CCCACTGCTC TGCCCCACCC TCCAATCTGC ACTTTGATTT GCTTCCTAAC
2451 AGCTCTGTTC CCTCCTGCTT TGGTTTTAAT AAATATTTTG ATGACGTTAA
2501 AAAAAGGAAT TCGATAT |
| SEQ ID NO.: 2 is 1766 base pair complementary DNA (cDNA) sequence encoding for wild-type E2F2 transcription factor isolated from a human HeLA S3 cDNA library. |
| 1 CAGGACTAGA GAGCGAGCCG CAAGGAAGTC GGTGCAGTCG AGACCCCCCT
51 CCCCATCCCA GCGCATCGCG TCTCCGCCGA GCTTGAGGGC ACGCCGGGGA
101 CCCCTCCCCA GAGCCGGCCG GACCCCAGGT GCCGAGGCCT TGGGGAGCGC
151 GGGGCGTCCC GGGTCGCGGT GCCCTCGGGA CGAGACAGCC CCTGGCAGTG
201 CCACCACCGC AGCCGCCGGG CGATCTCCAA GCGGCGATCT CTAAGCGCTG
251 CTCTCTGCTC GGCCGCGGGC CAGGAGGGGA GGGTCCGGCC TTGCCCCGCA
301 GGCGTCCATT GGCGGCTTCC CCCGCCTCC GCGCCATGCC GCGGGCCGTG
351 TGAAAGGCGG CAGCACCGGA ACCCGCAGGT GTCCGCGGGC GCGCCAAGCC
401 CTTTTGGGTA GGGGGCGCCT TACTCGCTAT GCTGCAAGGG CCCCGGGCCT
451 TGGCTTCGGC CGCTGGGCAG ACCCCGAAGG TGGTGCCCGC GATGAGCCCC
501 ACAGAGCTGT GGCCATCCGG CCTCAGCAGC CCCCAGCTCT GCCCAGCTAC
551 TGCTACCTAC TACACACCGC TGTACCCGCA GACGGCGCCT CCCGCAGCGG
601 CGCCAGGCAC CTGCCTCGAC GCCACTCCCC ACGGACCCGA GGGCCAAGTT
651 GTGCGATGCC TGCCGGCAGG CCGGCTGCCG GCCAAAAGGA AGCTGGATCT
701 GGAGGGGATT GGGAGGCCCG TCGTCCCTGA GTTCCCAACC CCCAAGGGGA
751 AGTGCATCAG AGTGGATGGC CTCCCCAGCC CCAAAACCCC CAAATCCCCC
801 GGGGAGAAGA CTCGGTATGA CACTTCGCTG GGGCTGCTCA CCAAGAAGTT
851 CATTTACCTC CTGAGCGAGT CAGAGGATGG GGTCCTGGAC CTGAACTGGG
901 CCGCTGAGGT GCTGGACGTG CAGAAGCGGC GCATCTATGA CATCACCAAC
951 GTGCTGGAAG GCATCCAGCT CATCCGCAAG AAGGCCAAGA CAACATCCA
1001 GTGGGTAGGC AGGGGAATGT TTGAAGACCC CACCAGACCT GGGAAGCAGC
1051 AACAGCTGGG GCAGGAGCTG AAGGAGCTGA TGAACACGGA GAGGCCTTG
1101 GACCAGCTCA TCCAGAGCTG CTCTCTGAGC TTCAAGCACC TGACTGAGGA
1151 CAAGGCCAAC AAGAGGCTGG CCTATGTGAC TTACCAGGAT ATCCGTGCTG
1201 TTGGCAACTT TAAGGAGCAG ACAGTGATTG CCGTCAAGGC CCCTCCGCAG
1251 ACGAGACTGG AAGTGCCCGA CAGGACTGAG GACAACCTGC AGATATATCT
1301 CAAGAGCACC CAAGGGCCCA TCGAAGTCTA CCTGTGCCCA GAGGAGGTGC
1351 AGGAGCCGGA CAGTCCTTCC GAGGAGCCTC TCCCCTCTAC CTCCACCCTC |

LIST OF THE SEQUENCES

```
1401 TGCCCCAGCC CTGACTCTGC CCAGCCCAGC AGCAGCACCG ACCCTAGCAT
1451 CATGGAGCCC ACAGCATCCT CAGTGCCAGC ACCAGCGCCA ACCCCCAGC
1501 AGGCCCCACC GCCTCCATCC CTGGTCCCCT TGGAGGCTAC TGACAGCCTG
1551 CTGGAGCTGC CGCACCCACT CCTGCAGCAG ACTGAGGACC AGTTCCTGTC
1601 CCCGACCCTG GCGTGCAGCT CCCCTCTGAT CAGCTTCTCC CCATCCTTGG
1651 ACCAGGACGA CTACCTGTGG GGCTTGGAGG CGGGTGAGGG CATCAGCGAT
1701 CTCTTCGACT CCTACGACCT TGGGGACCTG TTGATTAATT GAGTGGCCCT
1751 GCCTGCCCCC AGCAGC
```

SEQ ID NO. 3 is 1333 base pair complementary DNA (cDNA) sequence encoding for wild-type E2F4 transcription factor isolated from human fetal liver cells.

```
   1 GCGCGGAAGT GGCGCGGCGC GCCTGGCCTG GCCTGGCTGA GGGGAGGCGG
  51 CGGGCGGGCG CGATGGCGGA GGCCGGGCCA CAGGCGCCGC CGCCCCCGGG
 101 CACTCCAAGC CGGCACGAAA AGAGCCTGGG ACTGCTCACC ACCAAGTTCG
 151 TGTCCCTTCT GCAGGAGGCC AAGGACGGCG TGCTTGACCT CAAGCTGGCA
 201 GCTGACACCC TAGCTGTACG CCAGAAGCGG CGGATTTACG ACATTACCAA
 251 TGTTTTGGAA GGTATCGGGC TAATCGAGAA AAAGTCCAAG AACAGCATCC
 301 AGTGGAAGGG TGTGGGGCCT GGCTGCAATA CCCGGGAGAT TGCTGACAAA
 351 CTGATTGAGC TCAAGGCAGA GATCGAGGAG CTGCAGCAGC GGGAGCAAGA
 401 ACTAGACCAG CACAAGGTGT GGGTGCAGCA GAGCATCCGG AACGTCACAG
 451 AGGACGTGCA GAACAGCTGT TTGGCCTACG TCACTCATGA GGACATCTGC
 501 AGATGCTTTG CTGGAGATAC CCTCTTGGCC ATCCGGGCCC CATCAGGCAC
 551 CAGCCTGGAG GTGCCCATCC CAGAGGGTCT CAATGGGCAG AAGAAGTACC
 601 AGATTCACCT GAAGAGTGTG AGTGGTCCCA TTGAGGTTCT GCTGGTGAAC
 651 AAGGAGGCAT GGAGCTCACC CCCTGTGGCT GTGCCTGTGC CACCACCTGA
 701 AGATTTGCTC CAGAGCCCAT CTGCTGTTTC TACACCTCCA CCTCTGCCCA
 751 AGCCTGCCCT AGCCCAGTCC CAGGAAGCCT CACGTCCAAA TAGTCCTCAG
 801 CTCACTCCCA CTGCTGTCCC TGGCAGTGCA GAAGTCCAGG GAATGGCTGG
 851 CCCAGCAGCT GAGATCACAG TGAGTGGCGG CCCTGGGACT GATAGCAAGG
 901 ACAGTGGTGA GCTCAGTTCA CTCCCACTGG GCCCAACAAC ACTGGACACC
 951 CGGCCACTGC AGTCTTCTGC CCTGCTGGAC AGCAGCAGCA GCAGCAGCAG
1001 CAGCAGCAGC AGCAGCAGCA ACAGTAACAG CAGCAGTTCG TCCGGACCCA
1051 ACCCTTCTAC CTCCTTTGAG CCCATCAAGG CAGACCCCAC AGGTGTTTTG
1101 GAACTCCCCA AAGAGCTGTC AGAAATCTTT GATCCCACAC GAGAGTGCAT
1151 GAGCTCGGAG CTGCTGGAGG AGTTGATGTC CTCAGAAGTG TTTGCCCCTC
1201 TGCTTCGTCT TTCTCCACCC CCGGGAGACC ACGATTATAT CTACAACCTG
1251 GACGAGAGTG AAGGTGTCTG TGACCTCTTT GATGTGCCTG TTCTCAACCT
1301 CTGACTGACA GGGACATGCC CTGTGTGGCT GG
```

SEQ ID NO.: 4 Is a mutant E2F1a polynucleotide which is missing those nucleotides that encode amino acids 197–437 of the E2F1 wild-type (SEQ ID NO.: 1). The ATG represents the start codon (methionine) at position 136 of E2F1 [Genbank Sequence Number M95677 (Helin et al.1 infra)]

```
     ATGGC CTTGGCCGGG
 151 GCCCCTGCGG GCGGCCCATG CGCGCCGGCG CTGGAGGCCC TGCTCGGGGC
 201 CGGCGCGCTG CGGCTGCTCG ACTCCTCGCA GATCGTCATC ATCTCCGCCG
 251 CGCAGGACGC CAGCGCCCCG CCGGCTCCCA CCGGCCCCGC GGCGCCCGCC
 301 GCCGGCCCCT GCGACCCTGA CCTGCTGCTC TTCGCCACAC CGCAGGCGCC
 351 CCGGCCCACA CCCAGTGCGC CGCGGCCCGC GCTCGGCCGC CCGCCGGTGA
 401 AGCGGAGGCT GGACCTGGAA ACTGACCATC AGTACCTGGC CGAGAGCAGT
 451 GGGCCAGCTC GGGGCAGAGG CCGCCATCCA GGAAAAGGTG TGAAATCCCC
 501 GGGGGAGAAG TCACGCTATG AGACCTCACT GAATCTGACC ACCAAGCGCT
 551 TCCTGGAGCT GCTGAGCCAC TCGGCTGACG GTGTCGTCGA CCTQAACTGG
 601 GCTGCCGAGG TGCTGAAGGT GCAGAAGCGG CGCATCTATG ACATCACCAA
 651 CGTCCTTGAG GGCATCCAGC TCATTGCCAA GAAGTCCAAG AACCACATCC
 701 AGTGGCTGGG CAGCCACACC ACATGA
```

SEQ ID NO.: 5 is a mutant E2F1b polynucleotide which is missing those nucleotides that encode amino acids 128–181 and amino acids 409–426 of E2F1 wild-type (SEQ ID NO.: 1). The ATG represents the start codon (methionine) at position 136 of E2F1 [Genbank Sequence Number M95677 (Helin et al., infra)]

```
     ATGGC CTTGGCCGGG
 151 GCCCCTGCGG GCGGCCCATG CGCGCCGGCG CTGGAGGCCC TGCTCGGGGC
 201 CGGCGCGCTG CGGCTGCTCG ACTCCTCGCA GATCGTCATC ATCTCCGCCG
 251 CGCAGGACGC CAGCGCCCCG CCGGCTCCCA CCGGCCCCGC GGCGCCCGCC
 301 GCCGGCCCCT GCGACCCTGA CCTGCTGCTC TTCGCCACAC CGCAGGCGCC
 351 CCGGCCCACA CCCAGTGCGC CGCGGCCCGC GCTCGGCCGC CCGCCGGTGA
 401 AGCGGAGGCT GGACCTGGAA ACTGACCATC AGTACCTGGC CGAGAGCAGT
 451 GGGCCAGCTC GGGGCAGAGG CCGCCATCCA GGAAAAGGTG TGAAATCCCC
 501 GGGGGAGAAG TCACGCGCCAA GAAGTCCAAG AACCACATCC
 701 AGTGGCTGGG CAGCCACACC ACAGTGGGCG TCGGCGGACG GCTTGAGGGG
 751 TTGACCCAGG ACCTCCGACA GCTGCAGGAG AGCGAGCAGC AGCTGGACCA
 801 CCTGATGAAT ATCTGTACTA CGCAGCTGCG CCTGCTCTCC GAGGACACTG
 851 ACAGCCAGCG CCTGGCCTAC GTGACGTGTC AGGACCTTCG TAGCATTGCA
```

LIST OF THE SEQUENCES

```
 901 GACCCTGCAG AGCAGATGGT TATGGTGATC AAAGCCCCTC CTGAGACCCA
 951 GCTCCAAGCC GTGGACTCTT CGGAGAACTT TCAGATCTCC CTTAAGAGCA
1001 AACAAGGCCC GATCGATGTT TTCCTGTGCC CTGAGGAGAC CGTAGGTGGG
1051 ATCAGCCCTG GGAAGACCCC ATCCCAGGAG GTCACTTCTG AGGAGGAGAA
1101 CAGGGCCACT GACTCTGCCA CCATAGTGTC ACCACCACCA TCATCTCCCC
1151 CCTCATCCCT CACCACAGAT CCCAGCCAGT CTCTACTCAG CCTGGAGCAA
1201 GAACCGCTGT TGTCCCGGAT GGGCAGCCTG CGGGCTCCCG TGGACGAGGA
1251 CCGCCTGTCC CCGCTGGTGG CGGCCGACTC GCTCCTGGAG CATGTGCGGG
1301 AGGACTTCTC CGGCCTCCTC CCTGAGGAGT TCATCAGCCT TTCCCCACCC
1351 CACGAGGCCTGTGACT TTGGGGACCT CACCCCCCTG GATTTCTG
```

SEQ ID NO.: 6 is the deduced amino acid sequence of wild type E2F1 CDNA (SEQ ID NO.: 1).

MALAGAPAGG PCAPALEALL GAGALRLLDS SQJVIISAAQ DASAPPAPTG
PAAPAAGPCD PDLLLFATPQ APRPTPSAPR PALGRPPVKR RLDLETDHQY
LAESSGPARG RGRHPGKGVK SPGEKSRYET SLNLTTKRFL ELLSHSADGV
VDLNWAAEVL KVQKRRIYDI TNVLEGIQLI AKKSKNHIQW LGSHTTVGVG
GRLEGLTQDL RQLQESEQQL DHLMNJCTTQ LRLLSEDTDS QRLAYVTCQD
LRSIADPAEQ MMMVJKAPPE TQLQAVDSSE NFQISLKSKQ GPIDVFLCPE
ETVGGISPGK TPSQEVTSEE ENRATDSATI VSPPPSSPPS SLTTDPSQSL
LSLEQEPLLS RMGSLRAPVD EDRLSPLVAA DSLLEHVRED FSGLLPEEFI
SLSPPHEALD YHFGLEEGEG JRDLFDCDFG DLTPLDF

SEQ ID NO.: 7 is the deduced amino acid sequence of wild type E2F2 cDNA (SEQ ID NO.: 2).

MLQGPRALAS AAGQTPKVVPA MSPTELWPSG LSSPQLCPA TATYYTPLYP
QTAPPAAAPG TCLDATPHGPE GQVVRCLPAG RLPAKRKLD LEGJGRPVVP
EFPTPKGKCJ RVDGLPSPKT PKSPGEKTRY DTSLGLLTKK FIYLLSESED
GVLDLNWAAE VLDVQKRRJY DITNVLEGJQ LIRKKAKNNI QWVGRGMFED
PTRPGKQQQL GQELKELMNT EQALDQLJQS CSLSFKHLTE DKANKRLAYV
TYQDIRAVGN FKEQTVIAVK APPQTRLEVP DRTEDNLQIY LKSTQGPIEV
YLCPEEVQEP DSPSEEPLPS TSTLCPSPDS AQPSSSTDPS JMEPTASSVP
APAPTPQQAP PPPSLVPLEA TDSLLELPHP LLQQTEDQFL SPTLACSSPL
JSFSPSLDQD DYLWGLEAGE GJSDLFDSYD LGDLLJN

SEQ ID NO.: 8 is the deduced amino acid sequence of wild type E2F4 cDNA (SEQ ID NO.: 3)

MAEAGPQAPP PPGTPSRHEK SLGLLTTKFV SLLQEAKDGV LDLKLAADTL
AVRQKRRIYD JTNVLEGJGL JEKKSKNSJQ WKGVGPGCNT REIADKLJEL
KAEJEELQQR EQELDQHKVW VQQSJRNVTE DVQNSCLAYV THEDJCRCFA
GDTLLAJRAP SGTSLEVPJP EGLNGQKKYQ JHLKSVSGPJ EVLLVNKEAW
SSPPVAVPVP PPEDLLQSPS AVSTPPPLPK PALAQSQEAS RPNSPQLTPT
AVPGSAEVQG MAGPAAEJTV SGGPGTDSKD SGELSSLPLG PTTLDTRPLQ
SSALLDSSSS SSSSSSSSSN SNSSSSSGPN PSTSFEPJKA DPTGVLELPK
ELSEJFDPTR ECMSSELLEE LMSSEVFAPL LRLSPPPGDH DYJYNLDESE
GVCDLFDVPVL NL

SEQ ID NO.: 9 is a mutant E2F1a oncoprotein whose amino acid sequence is deduced from SEQ ID NO.: 4.

MALAGAPAG GPCAPALEAL LGAGALRLLD SSQIVIISAA QDASAPPAPT
GPAAPAAGP CDPDLLLFAT PQAPRPTPSA PRPALGRPPV KRRLDLETDH
QYLAESSGP ARGRGRHPGK GVKSPGEKSR YETSLNLTTK RFLELLSHSA
DGVVDLNWA AEVLKVQKRR IYDITNVLEG IQLIAKKSKN HJQWLGSHTT

SEQ ID NO.: 10 is a mutant E2F1b oncoprotein whose amino acid sequence is deduced froin SEQ ID NO.: 5.

MALAGAPAGG PCAPALEALL GAGALRLLDS SQIVIISAAQ DASAPPAPTG
PAAPAAGPCD PDLLLFATPQ APRPTPSAPR PALGRPPVKR RLDLETDHQY
LAESSGPARG RGRHPGKGVK SPGEKSRKKS KNHIQWLGSH TTVGVGGRLE
GLTQDLRQLQ ESEQQLDHLM NICTTQLRLL SEDTDSQRLA YVTCQDLRSI
ADPAEQMVMV IKAPPETQLQ AVDSSENFQI SLKSKQGPID VFLCPEETVG
GISPGKTPSQ EVTSEEENRA TDSATIVSPP PSSPPSSLTT DPSQSLLSLE
QEPLLSRMGS LRAPVDEDRL SPLVAADSLL EHVREDFSGL LPEEFJSLSP
PHEACDFGDL TPLDF

SEQ ID NO.: 11 is one of an oligonucleotide primer pair used in site-directed mutagenesis:

CCGGGGAGAAGTCACGCGCTAGCGCCAAGAAGTCCAAGAAC

SEQ ID NO.: 12 is the second of an oligonucleotide primer pair used in site-directed mutagenesis:

TCCCCACCCCACGAGGCCGCTAGCTGTGACTTTGGGGACCTC

DETAILED DESCRIPTION OF THE PREFERRED EMBODIMENT

One aspect of the present invention is based, in part, on our development of particular mutant E2F proto-oncogene sequences, which encode mutant E2F oncoprotein transcription factors. We have discovered that certain of these mutant E2F proto-oncogene sequences encode mutant transcriptional activators and will behave as dominant interfering transcriptional repressors in tumor cells that lack functional RB genes. Previously, we demonstrated that introduction of E2F1 mutants defective for transcriptional activation into tumor cells overrode RB-induced G0/G1 growth arrest. See Qin et al., *Mol. Cell. Biol.*, 15: 742–755 (1995), incorporated herein by reference. Therefore, it is quite surprising to find that transfection of E2F1 mutants by themselves into RB (−/−) cells is sufficient to inhibit tumor growth. See Example 1.

Definitions. In the description, the following terms are employed:

"Polynucleotide"—a polymer of nucleic acid monomeric units, the monomeric units being either ribonucleic acids (RNA), deoxyribonucleic acids (DNA), or combinations of both. The four DNA bases are adenine (A), guanine (G), cytosine (C) and thymine (T). The four RNA bases are A,G, C, and uracil (U).

"oncoprotein"—a protein encoded by a proto-oncogene

"gene"—a DNA sequence (i.e., a linear array of nucleotides connected to each other by 3'-5' pentose phosphodiester bonds) which encodes through its mRNA an amino acid sequence of a specific protein.

"transcription"—the process of producing mRNA from a gene.

"translation"—the process of producing a protein from mRNA.

"expression"—the process undergone by a DNA sequence or a gene to produce a protein, combining transcription and translation.

"proto-oncogene"—a gene that functions in normal cellular development which, if altered in an appropriate manner (i.e., elevation of expression level and mutational activation), can also serve to promote malignant development.

"inhibiting growth"—as used herein this term refers to both the inhibition of target cell (i.e.,tumor) growth and inhibition of the transformed phenotype (as measured by, for example, cell cycle arrest and changes in morphology).

"E2F family"—E2F is a cellular transcription factor originally identified through its role in transcriptional activation of the adenovirus E2 promoter. Kosvedi et al., *Cell*, 45: 219–228 (1986). As defined herein, polynucleotide members of the E2F family encode any protein that has at least one of the following biological properties.

1. the protein can transactivate the adenovirus E2 promoter in an E1A dependent manner;
2. the protein can bind to consensus E2F sites;
3. the carboxy teminal 60 kD portion of RB protein is associated with the E2F protein and this interaction is antagonized by adenovirus E1A and human papillomavirus E7 peptides (Hiebert et al., *Genes Dev.*, 6: 177–185 (1992) and binds to the product of the adenovirus E4 allele;
4. the protein contains potential C-terminal transactivating amino acid sequences that active transcription of known E2F-responsive genes (c-myc) in a manner that is dependent on the presence of one or more intact E2F binding sites and contains an N-terminal DNA binding domain;
5. the protein forms complexes with cellular proteins which are known to regulate cell cycle progression, like the pRB and pRB-related proteins p107 and p130;
6. the protein binds to DNA in vivo as heterodimers with members of the DP family of proteins (Neuman et al., *Mol. Cell. Biol.* 14: 6607–6615 (1994);
7. the protein binds to unphosphorylated RB protein both in vitro and in vivo and this binding can be competed for by adenovirus E1A;
8. the protein's highest regions of identity map to regions of the E2F1 protein that are known to be required either for DNA binding, pRB binding or transcriptional activation (Lees et al., *Mol. Cell. Biol.*, 13: 7813–7825 (1993).

"amino acid"—a monomeric unit of a peptide, polypeptide, or protein. There are twenty L-isomers of amino acids. The term also includes analogs of the amino acids and D-isomers of the protein amino acids and their analogs.

"protein"—any polymer consisting essentially of any of the 20 protein amino acids, regardless of its size. Although "polypeptide" is often used in reference to relatively large polypeptides, and "peptide" is often used in reference to small polypeptides, usage of these terms in the art overlaps and is varied. The term "protein" as used herein refers to peptides, proteins and polypeptides, unless otherwise noted.

"genetic fusion"—refers to a co-linear, covalent linkage of two or more proteins via their individual peptide backbones, through genetic expression of a polynucleotide molecule encoding those proteins.

"mutant"—any change in quantity or structure of genetic material of an organism, in particular any change (i.e., deletion, substitution, addition, or alteration) in a wild type proto-oncogene or any change in a wild type oncoprotein.

"dominant interfering mutant"—a mutated gene encoding a mutated protein which lacks the activity of the wild-type protein but which also inhibits activity of the wild-type protein when co-expressed along with the wild-type protein.

"wild type"—the naturally-ocurring polynucleotide or amino acid sequence of a proto-oncogene or oncoprotein, respectively, as it exists in vivo.

"standard hybridization conditions"—salt and temperature conditions substantially equivalent to 0.5× SSC to about 5× SSC and 65 degrees C. for both hybridization and wash. The term "standard hybridization conditions" as used herein is therefore an operational definition and encompasses a range of hybridization. Higher stringency conditions may, for example, include hybridizing with plaque screen buffer (0.2% polyvinylpyrrolidone, 0.2% Ficoll 400; 0.2% bovine serum albumin, 50 mM Tris-HCl (pH 7.5); 1M NaCl; 0.1% sodium pyrophosphate; 1% SDS); 10% dextran sulphate, and 100 ug/ml denatured, sonicated salmon sperm DNA at 65 degrees C. for 12–20 hours, and washing with 75 mM NaCl/7.5 mM sodium citrate (0.5× SSC)/1% SDS at 65 degrees C. Lower stringency conditions may, for example, include hybridizing with plaque screen buffer, 10% dextran sulphate and 110 ug/ml denatured, sonicated salmon sperm DNA at 55 degrees C. for 12–20 hours, and washing with 300 mM NaCl/30 mM sodium citrate (2.0× SSC)/1% SDS at 55 degrees C.

"expression control sequence"—a sequence of nucleotides that controls and regulates expression of genes when operatively linked to those genes.

"operatively linked"—a polynucleotide sequence (DNA, RNA) is operatively linked to an expression control sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the polynucleotide sequence under the control of the expression control sequence and production of the desired mutant oncoprotein encoded by the polynucleotide sequence.

"expression vector"—a polynucleotide, most commonly a DNA plasmid, which allows expression of at least one gene when the expression vector is introduced into a host cell. The vector may, or may not, be able to replicate in a cell.

"tumor"—any undesireable proliferation of cells. Such growth includes malignant and non-malignant, solid or fluid tumors, carcinomas, myelomas, sarcomas, leukemias, lymphomas and other cancerous, neoplastic or tumorigenic diseases.

Isolated, Mutant Polynucleotides

"Isolated", when applied to polynucleotide sequences of mutant proto-oncogenes that encode mutant oncoproteins, means an RNA or DNA polynucleotide, portion of genomic polynucleotide, cDNA or synthetic polynucleotide which, by virtue of its origin or manipulation: (i) is not associated with all of a polynucleotide with which it is associated in nature (e.g., is present in a host cell as a portion of an expression vector); or (ii) is linked to a nucleic acid or other chemical moiety other than that to which it is linked in nature; or (iii) does not occur in nature. By "isolated" it is further meant a polynucleotide sequence: (i) amplified in vitro by, for example, polymerase chain reaction (PCR); (ii) chemically synthesized; (iii) recombinantly produced by cloning; or (iv) purified, as by cleavage and gel separation.

Preferred mutant proto-oncogene polynucleotides that may be used to inhibit tumor cell growth according to the methods of the invention are derived from the wild-type E2F1 transcription factor (SEQ ID NO.: 1) See Helin et al., "A cDNA encoding a pRB-binding protein with properties of the transcription factor E2F", *Cell* 70, 337–350, 1992, incorporated herein by reference. SEQ ID NO.: 1 is a 2517 base pair complementary DNA (cDNA) sequence encoding for E2F1 transcription factor isolated from a lambda expression library. An open reading frame of 1313 base pairs is identified from nucleotides 1 to 2517 of SEQ ID NO.: 1. Numbering of nucleotides follows the convention of starting with the first base [pair] (G) of SEQ ID NO.: 1 as base number 1. Other members of the E2F family are presented as wild-type E2F2 polynucleotide (SEQ ID NO. 2), wild-type E2F4 polynucleotide (SEQ ID NO.: 3). Other members include E2F3 protein (Lees et al., *Mol. Cell. Biol.*, 13: 7813–7825, 1993) E2F4 protein (Hijmans et al., *Mol. Cell. Biol.*,15: 3082–3089, 1995) and E2F5 polynucleotide (Hijmans et al., id, GenBank X 86097) all of which are incorporated herein by reference.

Mutant members of the E2F family of transcription factor proto-oncogenes may be used in accordance with this invention. In particular, SEQ ID NO.: 4 is a mutant E2F1 proto-oncogene ("E2F1a") which is missing those polynucleotides encoding the transactivation domain, the RB binding domain, the leucine zipper sequence and the "marked" box domain (see discussion of oncoprotein domain structure, infra). SEQ ID NO.: 5 is a mutant E2F1 proto-oncogene ("E2F1b") which is missing those polynucleotides encoding part of the DNA binding domain and the entire RB binding domain, but retains those polynucleotides encoding the "marked" box region, which may interact with components of the cellular transcription and/or cell cycle machinery. Mutations in the wild-type E2F1 sequence are developed using conventional methods of directed mutagenesis, known to those of ordinary skill in the art.

The "design rules" for developing a particular mutant E2F proto-oncogene encoding a dominant interfering mutant of an oncoprotein may vary with the individual polynucleotide sequence. For E2F family members, alterations in the DNA binding domain and/or the RB binding domain (see supra) will likely produce dominant interfering mutants that act effectively to inhibit tumor growth. For example, mutant proto-oncogene polynucleotides derived from wild-type E2F4 (Hijmans et al., *Mol. Cell. Biol.*, 15: 3082–3089,1995) would lack those polynucleotides encoding amino acids 10–83 (DNA binding domain of wild-type E2F4 protein) and/or those polynucleotides encoding amino acids 382 to about 412 (RB binding domain of E2F4 protein). Other E2F4 protein mutants would retain those only polynucleotides capable of encoding amino acids 1 to about 181 of wild-type E2F4 (i.e, those that retain DNA binding activity). Similarly, mutant proto-oncogene polynucleotides derived from the wild-type E2F5 polynucleotide (Hijmans et al., supra) would likely lack those polynucleotides encoding amino acids 43 to about 115 (DNA binding domain of wild-type E2F5 protein) and/or those polynucleotides encoding amino acids 317 to about 346 (RB or RB-related protein binding domain of the E2F5 protein). Other E2F5 mutants would retain only those polynucleotides capable of encoding amino acids 1 to about 215 of wild-type E2F5 protein (the DNA binding domain). Such mutants may be created using no more than routine experimentation.

Moreover, the isolated, mutant polynucleotides depicted in SEQ ID NOS. 4–5 can be altered to provide for functionally equivalent polynucleotides. A polynucleotide is "functionally equivalent" compared with those of SEQ ID NOS.: 4–5 if it satisfies at least one of the following conditions: (a): the "functional equivalent" is a polynucleotide that hybridizes to any of the foregoing sequences (SEQ ID NOS.:4–5) under standard hybridization conditions. Most preferably, it encodes a mutant oncoprotein having the cell growth inhibition activity of a dominant interfering mutant of an E2F transcription factor;

(b) the "functional equivalent" is a polynucleotide that codes on expression for an amino acid sequence encoded by any of the polynucleotides of SEQ ID NOS. 4–5.

Due to the degeneracy of the nucleotide coding sequences, other polynucleotides may be used to encode dominant, interfering mutants of oncoproteins. For E2F1 oncoproteins these include all, or portions of SEQ ID NOS.: 4–5, which are altered by the substitution of different codons that encode the same amino acid residue within the sequence, thus producing a silent change. Such altered sequences are regarded as equivalents of SEQ ID NOS.: 4–5. For example, Phe(f) is coded for by two codons, TTC or TTT, Try (Y) is coded for by TAC or TAT and His (H) is coded for by CAC or CAT. On the other hand, Trp (W) is coded for by a single codon, TGG. Accordingly, it will be appreciated that for a given DNA sequence encoding a particular mutant oncoprotein there will be many DNA degenerate sequences that will code for it. These degenerate DNA sequences are considered within the scope of this invention.

Mutant E2F1 proto-oncogenes have been administered to a tumor cell via an expression vector and are able to inhibit growth of the tumor cells. See Example 1. Generally, one tests the efficacy of a given mutant on tumor cell growth and metabolism by assaying for: (i) alterations in cellular morphology (production of large cells); (ii) induction of G1 arrest; and/or (iii) inhibition of macroscopic colony formation. Methods for determining these properties of cells are described in Qin et al., *Mol. Cell. Biol.* 15: 742–755 (1995), incorporated herein by reference.

Isolated, Mutant Oncoproteins

"Isolated", when applied to mutant oncoproteins, means a protein, or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature. By "isolated" it is further meant a protein that is: (i) chemically synthesized; or (ii) expressed in a host cell and purified away from associated proteins, as by gel chromatography.

Wild type E2F1 cDNA (SEQ ID NO.:1) predicts a protein of 437 amino acids (SEQ ID NO.:6). Amino acid residues begin with the start codon (ATG) as residue number 1. SEQ ID NO.: 1 cDNA encodes an oncoprotein that contains several domains that are conserved among members of the E2F family. The first conserved region corresponds to an amino acid motif sequence at amino acids 89 to 95. The second conserved domain (amino acids 120 to 191) includes a helix-loop-helix motif and corresponds to a region of high sequence identity among E2F members, whose carboxy terminal region provides the primary residues required for E2F1 to bind to DNA. Another region of homology is a putative leucine zipper that spans amino acid residues 215 to 243 of E2F1. A third region of homology between E2F members is just carboxy terminal to the putative leucine zipper and has been termed the "marked box" region (amino acids 251 to 317 of E2F1). The last segment of homology is the extreme carboxy terminus and corresponds to the region necessary for transactivation and necessary for E2F1 to interact with the RB gene product (amino acids 409 to 426). Other protein members of the E2F family include wild type E2F2 (SEQ ID NO.: 7) wild type E2F4 (SEQ ID NO.: 8). See also Hijmans, supra for the E2F5 amino acid sequence and Lees et al., supra for the E2F3 amino acid sequence.

Mutant oncoprotein members of the E2F family of transcription factors may be used in accordance with this invention. In particular, SEQ ID NO.: 9 is a mutant E2F1a oncoprotein whose amino acid sequence is deduced from SEQ ID NO.: 4. This oncoprotein sequence lacks amino acids 197 through 437 of wild-type. SEQ ID NO.: 10 is a mutant E2F1b oncoprotein whose amino acid sequence is deduced from SEQ ID NO.: 5 and is missing amino acids 128–191 (within the DNA binding domain) and amino acids 409–426 (the RB binding domain.

Mutant E2F oncoproteins are not limited to those containing as a primary amino acid sequence those depicted, for instance, in SEQ ID NOS.: 9–10 but include altered sequences in which functionally equivalent amino acid residues are substituted for residues within the sequence, resulting in a silent change. A mutant oncoprotein is "functionally equivalent" to the oncoproteins of SEQ ID NOS.: 9–10 if the protein contains one or more amino acid residues with the protein which can be substituted by another amino acid of similar polarity which acts as a conservative substitution (i.e., a functional equivalent). In addition, substitutes for an amino acid with a mutant oncoprotein sequence may also be selected from other members of the class to which the amino acid belongs. The non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Generally, substitutions that may be expected to induce changes in the functional properties of mutant oncoproteins are those in which: (i) a hydrophilic residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative charge, e.g., glutamic acid or aspartic acid; or (iv) a residue having a bulky side chain, e.g., phenylalanine, is substituted for (or by) one not having such a side chain, e.g., glycine.

The oncogenic nature of E2F members is established by co-transfecting plasmids containing, for example, wild-type cDNA of E2F1, E2F2 or E2F5, and the like and an activated Ha-ras oncogene into primary rat embryo fibroblasts, and measuring: (i) morphologically transformed cells; (ii) E2F expression in the transformed cells, and (iii) the ability of the transformed cells to form tumors in nude mice. See Johnson et al., *Proc. Nat. Acad. Sci. USA*, 91:12823–12827 (1994), incorporated herein by reference. Alternately, a cDNA member of the E2F family may be placed under control of the constitutive promoter of cytomegalovirus and introduced directly into rat embryo fibroblasts in a drug-selectable vector. Stable transfectants are analysed for changes in morphology, growth characteristics and tumorigenicity in nude mice. See, for example, Singh et al., *EMBO J.*, 13: 3329–3338 (1994), incorporated herein by reference. Any member of the E2F family may be conveniently tested for oncogenic potential using these methods.

It will be readily appreciated by those having ordinary skill in the art that many other proto-oncogenes encode transcription factors and that mutants of these other proto-oncogenes may be generated using similar procedures to those used to generate E2F mutants. The DNA binding domain of transcription factor proto-oncogenes (Table 1) is usually easily identified. In particular, there are a few DNA binding motifs which are frequently found in these proteins. These include the leucine zipper/basic DNA binding domain (found in the fos and jun oncoproteins); the helix-loop-helix domain found in myc- which would be expected to form heterodimers like E2F; zinc fingers (found in erbA) and the homeobox domain (found in pbx). Thus, it is reasonably straightforward to design a dominant interfering mutant in the manner of our E2F mutants by deleting, for example, all portions of the proto-oncogene encoding these transcription factors except for those portion(s) of the well-defined DNA binding domain. Complete coding sequences of most identified proto-oncogenes have been sequenced and many are in Genbank. For instance, the human c-jun proto-oncogene is designated Gb_pr:Humjuna, number J04111; the human c-mym proto-oncogene is designated Gb_pr:Hsmcl and has accession number V00568. It will be understood that other proto-oncogene sequences may be obtained in the same manner.

TABLE I

| Proto-oncogene | Function of Oncoprotein |
|---|---|
| myc | Sequence specific DNA binding protein |
| mdm2 | Transcription factor for p 53 |

TABLE I-continued

| Proto-oncogene | Function of Oncoprotein |
| --- | --- |
| myb | Sequence specific DNA binding protein. |
| fos | Combines with jun product to form AP-1 transcription factor |
| jun | Sequence specific DNA binding protein; part of AP-1 |
| erbA | Dominant interfering mutant thyroxine (T3) receptor |
| N-myc | Sequence specific DNA binding protein |
| L-myc | Sequence specific DNA binding protein |

To provide a more detailed description of the design rules for generating dominant interfering mutants, we used the proto-oncogene mdm2. The mdm2 gene was first discovered to be amplified in transformed mouse cell lines and was later found to be tumorigenic when overexpressed. Fakharzadeh et al., *EMBO J*. 10:1565–1569 (1991), incorporated herein by reference. The mdm2 oncoprotein was found to form a complex with the tumor suppressor gene p53, resulting in inhibition of p53-mediated transcriptional activation. Momand et al., *Cell* 69: 1237–1245 (1992). Thus, mdm2 appears to affect the ability of p53 to suppress growth by inhibiting the transcriptional activity of p53. Human mdm2 which binds to p53 has been cloned and sequenced. Chen et al., *Mol. Cell. Biol.* 13:4107–4114 (1993), incorporated herein by reference. Amplification of human mdm2 gene has been found in many tumors, particularly sarcomas.

The human mdm2 oncoprotein (also called hdm2) has the following defined domains (see Chen et al., supra): an amino-terminal region which binds p53, followed by a nuclear localization sequence, a central acidic regions which may be a transactivation domain, and a carboxy-terminal zinc finger which may be a DNA binding domain. Two different human mdm2 mutants can be generated. In one case, the p53-binding domain (amino acids 19 to about 100) and the C-terminal zinc finger motif (DNA binding domain) are deleted. In another mutant, the same p53-binding domain is deleted along with a deletion of the acidic, transactivation domain (amino acids 211 to about 297). Alternately, these domains may be crippled by site-specific mutation rather than deletion.

The mutant proto-oncogenes are inserted into a mammalian cell expression vector and tested by transfection into cultured cells. Two different tests are performed. In an experiment similar to that of Momand et al., (supra), the ability of the encoded mutant oncoproteins to block mdm2-mediated p53 inhibition is analyzed. Mdm2 mutants are co-transfected along with wild-type mdm2. This experiment will determine if the mutants can inhibit the activity of mdm2. In a second experiment, the ability of the mdm2 mutants to encode mutant oncoproteins that inhibit the growth of p53-negative tumor cell lines (i.e., colon cancer cells) can be analyzed in a manner similar to those described in Example 1.

Production and Expression of Mutant Oncoproteins

The mutant oncoproteins described herein can be produced by any suitable method known in the art. Such methods include constructing a DNA sequence encoding mutant oncoprotein sequences and expressing those sequences in a suitable transformed host. This method will produce isolated, mutant oncoproteins. For example, E2F2 cDNA may be isolated by screening a human cDNA library with a labeled DNA fragment of E2F1 and identifying positive clones by autoradiography. Further rounds of plaque purification and hybridization are performed using conventional methods. See Ivey-Hoyle et al., *Mol. Cell. Biol.*, 13:7802–7812 (1993), incorporated herein by reference. Similar, well-established methods may be used to isolate E2F3 cDNA (Lees et al., *Mol. Cell. Biol.*, 13: 7813–7825, 1993), as well as E2F4 and E2F5 cDNA (Sardet et al., *Proc. Nat. Acad. Sci. USA*, 92:2403–2407, 1995; Hijmans et al., supra), incorporated herein by reference.

However, the mutant oncoproteins may also be produced, albeit less preferably, by chemical synthesis or a combination of chemical synthesis and recombinant DNA technology. In one embodiment of a recombinant method for producing a mutant E2F oncoprotein, a DNA sequence is constructed by isolating or synthesizing a DNA sequence encoding wild type E2F1 (see SEQ ID NO.: 1) and then mutagenizing by site-specific mutagenesis. See, e.g., Zoeller et al., "Site-specific Mutagenesis Of The Human Fibroblast Interferon Gene", *Proc. Natl. Acad. Sci. USA*, 81, pp. 5662–66 (1984); U.S. Pat. No. 4,588,585, incorporated herein by reference. Complementary DNA sequences of E2F family members are known. See, supra. Other E2F family members, not yet known, may also be isolated using conventional recombinant DNA procedures and mutagenized using routine methods and our design rules.

Another method of constructing a DNA sequence encoding mutant oncoproteins would be by chemical synthesis. For example, a mutant mdm2 proto-oncogene (see Chen et al, supra) or an E2F polynucleotide which encodes the desired mutant oncoprotein (e.g., a polynucleotide encoding an E2F4 protein lacking amino acids 10–83; the DNA binding domain) may be synthesized by chemical means using an oligonucleotide synthesizer. Such oligonucleotides are designed based on the amino acid sequence of the desired oncoprotein, and preferably selecting those codons that are favored in the host cell in which the recombinant oncoprotein will be produced.

The DNA sequence encoding mutant oncoproteins, whether prepared by site directed mutagenesis, synthesis or other methods, may or may not also include DNA sequences that encode a signal sequence. The inclusion of a signal sequence depends on whether it is desired to secrete the oncoprotein from the recombinant cells in which it is made. If the cells chosen to provide the expression host are prokaryotic, it generally is preferred that the DNA sequence not encode a signal sequence.

Standard methods may be applied to synthesize a polynucleotide sequence encoding a mutant oncoprotein. For example, a complete amino acid sequence may be used to construct a back-translated gene. Deduced amino acid sequences for five members of the E2F family are known. See, Kaelin et al., supra, Ivey-Hoyle et al., supra and UK Publication GB 2282814A: 19 Apr., 1995, Lees et al., supra, Sardet et al., supra and Hijmans et al., supra. Further, a DNA oliqomer containing a nucleotide sequence coding for the particular mutant oncoprotein may be synthesized. For example, several small oligonucleotides coding for portions of the desired polypeptide may be synthesized and then ligated. The individual oligonucleotides typically contain 5' or 3' overhangs for complementary assembly.

Once assembled (by synthesis, site directed mutagenesis or another method), the mutant DNA sequences encoding a mutant oncoprotein will be inserted into an expression vector and operatively linked to an expression control sequence appropriate for expression of the oncoprotein in a desired host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The choice of expression control sequence and expression vector will depend upon the choice of host. A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including col E1, pCR1, pBR322, pMB9 and their derivatives, wider host range plasmids, such as M13 and filamentous single stranded DNA phages. Preferred *E. coli* vectors include pL vectors containing the lambda phage pL promoter (U.S. Pat. No. 4,874,702), pET vectors containing the T7 polymerase promoter (Studier et al., *Methods in Enzymology* 185: 60–89, 1990) and the pSP72 vector (Kaelin et al., supra). Useful expression vectors for yeast cells include the $2\mu$ plasmid and derivatives thereof. Useful vectors for insect cells include pVL 941. In addition, any of a wide variety of expression control sequences may be used in these vectors. Such useful expression control sequences include the expression control sequences associated with structural genes of the foregoing expression vectors. Examples of useful expression control sequences include, for example, the early and late promoters of SV40 or adenovirus, the lac system, the trp system, the TAC or TRC system, the major operator and promoter regions of phage lambda, for example pL, the control regions of fd coat protein, the promoter for 3-phosphoglycerate kinase or other glycolytic enzymes, the promoters of acid phosphatase, e.g., Pho5, the promoters of the yeast α-mating system and other sequences known to control the expression of genes or prokaryotic or eukaryotic cells and their viruses, and various combinations thereof.

Any suitable host may be used to produce in quantity the oncoproteins described herein, including bacteria, fungi (including yeasts), plant, insect, mammal, or other appropriate animal cells or cell lines, as well as transgenic animals or plants. More particularly, these hosts may include well known eukaryotic and prokaryotic hosts, such as strains of *E.coli*, Pseudomonas, Bacillus, Streptomyces, fungi, yeast, insect cells such as *Spodoptera Frugiperda* (SF9), and animal cells such as Chinese hamster ovary (CHO) and mouse cells such as NS/O, African green monkey cells such as COS1, COS 7, BSC 1, BSC 40, and BMT 10, and human cells, as well as plant cells in tissue culture. For animal cell expression, we prefer CHO cells and COS 7 cells in cultures.

It should of course be understood that not all vectors and expression control sequences will function equally well to express a given mutant oncoprotein. Neither will all hosts function equally well with the same expression system. However, one of skill in the art may make a selection among these vectors, expression control systems and hosts without undue experimentation. For example, to produce mutant oncoproteins of the E2F family in large scale animal culture, the copy number of the expression vector must be controlled. Amplifiable vectors are well known in the art. See, for example, U.S. Pat. Nos. 4,470,461 and 5,122,464; Kaufman and Sharp, *Mol. Cell. Biol.*, 2: 1304–1319 (1982). The mutant E2F oncoproteins produced by a transformed host can be purified according to any suitable method.

Conjugated/Modified Oncoproteins

Mutant oncoproteins may also be chemically modified to facilitate its delivery to a target cell. One such modification involves increasing the lipophilicity of the oncoprotein in order to increase cell surface binding and stimulate non-specific endocytosis of the oncoprotein. A wide variety of lipopeptides, fatty acids, and basic polymers (e.g., tripalmitoyl-S-glycerylcysteil-seryl-serine; palmitic acid; polyarginine) may be linked to a mutant oncoprotein to accomplish this. See U.S. Pat. No. 5, 219,990, incorporated herein by reference. Mutant oncoproteins may also be modified to increase their resistance to proteases by incorporating D-amino acids instead of L-amino acids at some or all amino acid residues. See, U.S. Pat. No. 5,219,990 supra.

Delivery may also be effected by using carrier moieties known to cross cell membranes. For example, an oncoprotein such as a mutant E2F1 transcriptional factor may be fused to a carrier moeity, preferably by genetic fusion, and the fused construct may be expressed in bacteria or yeast using standard techniques. Thus, polynucleotide sequences encoding mutant oncoproteins useful in the present invention, operatively linked to regulatory sequences, may be constructed and introduced into appropriate expression systems using conventional recombinant DNA techniques. The resulting fusion protein may then be purified and tested for its capacity to enter intact target cells and inhibit growth of the target cells once inside the target. For example, recombinant methods may be used to attach a carrier moiety to mutant E2F sequences by joining the polynucleotide sequence encoding for mutant E2F oncoprotein with the polynucleotide sequence encoding a carrier moiety and introducing the resulting construct into a cell capable of expressing the conjugate. Two separate sequences may be synthesized, either by recombinant means or chemically, and subsequently joined using known methods. The entire conjugate may be chemically synthesized as a single amino acid sequence.

Useful carrier moieties include, for example, bacterial hemolysins or "blending agents" such as alamethicin or sulfhydryl activated lysins. Other carrier moieties include cell entry components of bacterial toxins such as Pseudomonas exotoxin, tetanus toxin, ricin toxin and diphtheria toxin. Other useful carrier moieties include proteins which are viral receptors, cell receptors or cell ligands for specific receptors that are internalized and cross mammalian cell membranes via specific interaction with cell surface receptors. Such cell ligands include epidermal growth factor, fibroblast growth factor, transferrin and platelet derived growth factor. The carrier moiety may also include bacterial immunogens, parasitic immunogens, viral immunogens, immunoglobulins, cytokines.

In a preferred embodiment, purified human immunodeficiency virus type-1 (HIV) tat protein is the carrier moiety. Purified human immunodeficiency virus type-1 (HIV) tat protein is taken up from the surrounding medium by human cells growing in culture. See Frankel et al., *Cell* 55: 1189–1193, (1988); Fawell et al., *Proc. Nat. Acad. Sci., USA* 91: 664–668 (1994) (use of tat conjugate); and Pepinsky et al., *DNA and Cell Biology*, 13: 1011–1019 (1994) (use of tat genetic fusion construct), all of which are incorporated herein by reference. See also co-pending and commonly assigned PCT Application Serial Number PCT/US93/07833, published 3 Mar., 1994, incorporated herein by reference, which describes the tat-mediated uptake of the papillomavirus E2 repressor; utilizing a fusion gene in which the HIV-1 tat gene is linked to the carboxy-terminal region of the E2 repressor open reading frame.

The tat protein can deliver, for example, mutant E2F oncoproteins and mutant E2F proto-oncogene polynucleotide sequences into cells, either in vitro or in vivo. For example, delivery can be carried out in vitro by adding a genetic fusion encoding a dominant interfering mutant of an E2F oncoprotein-tat conjugate to cultured cells to produce cells that synthesize the tat conjugate or by combining a sample (e.g., blood, bone marrow, tumor cell) from an individual directly with the conjugate, under appropriate conditions. The target cells may be in vitro cells such as cultured animal cells, human cells or microorganisms. Delivery may be carried out in vivo by administering the mutant E2F molecule and tat protein to an individual in which it is to be used. The target may be in vivo cells, i.e., cells composing the organs or tissue of living animals or humans, or microorganisms found in living animals or humans. The ADP ribosylation domain from Pseudomonas exotoxin ("PE") and pancreatic ribonuclease have been conjugated to tat to confirm cytoplasmic delivery of a protein. The ADP phosphorylation domain is incapable of entering cells so that cytoplasmic delivery of this molecule would be confirmed if cell death occurs. Likewise, ribonuclease itself is incapable of entering cells so that inhibition of protein synthesis would be a hallmark of intracellular delivery using a tat conjugate.

Papillomavirus E2 repressor proteins have also been conjugated to tat and serve as a good test of the effectiveness of tat-E2F1 mutant oncoprotein conjugates of the invention. The papillomavirus E2 protein regulates both transcription and replication of the papillomavirus genome. Although transient expression in mammalian cells of DNA sequences encoding various analogs of E2 inhibits trans-activation of the full length protein (See Barsoum et al., *J. Virol.*, 66: 3941–3945, 1992), E2 repressors cannot enter mammalian cells. Conjugation of tat to E2 repressors results in transport into the cell where E2-dependent expression of a reporter gene is repressed. See Pepinsky et al., supra.

The entire 86 amino acids which make up the tat protein (See Pepinsky et al., supra) may be used although the entire protein may not be required. Smaller fragments may be tested for their ability to enter cells and effectively transfer polynucleotide or amino acid sequences into cells using no more than routine methods. See PCT Application Serial Number PCT/US93/07833, published 3 Mar., 1994.

Chemical (i.e., non-recombinant) attachment of mutant proto-oncogene sequences or mutant oncoprotein sequences to a carrier moiety may be effected by any means which produces a link between the two components which can withstand the conditions used and which does not alter the function of either component. Many chemical cross-linking agents are known and may be used to join a mutant proto-oncogene or oncoprotein to carrier moieties. Among the many intermolecular cross-linking agents are, for example, succinimidyl 3-(2-pyridyldithio)propionate (SPDP) or N, N'-(1,2-phenylene)bismaleimide are highly specific for sulfhydryl groups and form irreversible linkages; N, N'-ethylene-bis-(iodoacetamide) (specific for sulfhydryl); and 1,5-difluoro-2,4-dinitrobenzene (forming irreversible linkages with tyrosine and amino groups). Other agents include p,p'-difluoro-m,m'-dinitrodiphenylsulfone (forming irreversible linkages with amino and phenolic groups); dimethyl adipimidate (specific for amino groups); hexamethylenediisocyante (specific for amino groups); disdiazobenzidine (specific for tyrosine and histidine); succinimidyl 4-(N-maleimidomethyl)cyclohexane-1-carboxylate (SMCC); m-maleimidobenzoyl-N-hydroxysuccinimide ester (MBS); and succinimide 4-(p-maleimidophenyl)butyrate (SMPB).

The succinimidyl group of these cross-linkers reacts with a primary amine, and the thiol-reactive maleimide reacts with the thiol of a cysteine residue. See, Means and Feeney, Chemical Modification of Proteins, Holden-Day, 39–43, 1974; and S. S. Wong, Chemistry of Protein Conjugation and Cross-Linking, CRC Press, 1971. All the cross-linking agents discussed herein are commercially available and detailed instructions for their use are available from the suppliers.

Methods of Preparing Gene Therapy Vectors

Any of the methods known in the art for the insertion of polynucleotide sequences into a vector may be used. See, for example, Sambrook et al., Molecular Cloning: A Laboratory Manual, Cold Spring Harbor Laboratory, Cold Spring Harbor, N.Y. (1989) and Ausubel et al., Current Protocols in Molecular Biology, J. Wiley & Sons, NY (1992), both of which are incorporated herein by reference. Conventional vectors consist of appropriate transcriptional/translational control signals operatively linked to the polynucleotide sequence for a particular mutant proto-oncogene. Promoters/enhancers may also be used to control expression of mutant oncoproteins. Promoter activation may be tissue specific or inducible by a metabolic product or administered substance. Such promoters/enhancers include, but are not limited to, the native E2F promoter, the cytomegalovirus immediate-early promoter/enhancer (Karasuyama et al., *J. Exp. Med.*, 169: 13 (1989)); the human beta-actin promoter (Gunning et al., *Proc. Nat. Acad. Sci. USA*, 84: 4831 (1987); the glucocorticoid-inducible promoter present in the mouse mammary tumor virus long terminal repeat (MMTV LTR) (Klessig et al., *Mol. Cell. Biol.*, 4: 1354 (1984)); the long terminal repeat sequences of Moloney murine leukemia virus (MuLV LTR) (Weiss et al., RNA Tumor Viruses, Cold Spring Harbor Laboratory, Cold Spring Harbor, N.Y. (1985)); the SV40 early region promoter (Bernoist and Chambon, *Nature*, 290:304 (1981)); the promoter of the Rous sarcoma virus (RSV) (Yamamoto et al., *Cell*, 22:787 (1980)); the herpes simplex virus (HSV) thymidine kinase promoter (Wagner et al., *Proc. Nat. Acad. Sci. USA*, 78: 1441 (1981)); the adenovirus promoter (Yamada et al., *Proc. Nat. Acad. Sci. USA*, 82: 3567 (1985)).

Expression vectors compatible with mammalian host cells for use in gene therapy of tumor cells include, for example, plasmids; avian, murine and human retroviral vectors; adenovirus vectors; herpes viral vectors; and non-replicative pox viruses. In particular, replication-defective recombinant viruses can be generated in packaging cell lines that produce only replication-defective viruses. See Current Protocols in Molecular Biology: Sections 9.10–9.14 (Ausubel et al., eds.), Greene Publishing Associates, 1989.

Specific viral vectors for use in gene transfer systems are now well established. See for example: Madzak et al., *J. Gen. Virol.*, 73: 1533–36 (1992: papovavirus SV40); Berkner et al., *Curr. Top. Microbiol. Immunol.*, 158: 39–61 (1992: adenovirus); Moss et al., *Curr. Top. Microbiol. Immunol.*, 158: 25–38 (1992: vaccinia virus); Muzyczka, *Curr. Top. Microbiol. Immunol.*, 158: 97–123 (1992: adeno-associated virus); Margulskee, *Curr. Top. Microbiol. Immunol.*, 158: 67–93 (1992: herpes simplex virus (HSV) and Epstein-Barr virus (HBV)); Miller, *Curr. Top. Microbiol. Immunol.*, 158: 1–24 (1992: retrovirus); Brandyopadhyay et al., *Mol. Cell. Biol.*, 4: 749–754 (1984: retrovirus); Miller et al., *Nature*, 357: 455–450 (1992: retrovirus); Anderson, *Science*, 256: 808–813 (1992: retrovirus), all of which are incorporated herein by reference.

Preferred vectors are DNA viruses that include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., *Gene Therapy* 1: 367–384, 1994; U.S. Pat. Nos. 4,797,368 and 5,399,346 and discussion below.

The choice of a particular vector system for transferring, for instance, a mutant E2F proto-oncogene sequence will depend on a variety of factors. One important factor is the nature of the target cell population. Although retroviral vectors have been extensively studied and used in a number of gene therapy applications, they are generally unsuited for infecting cells that are not dividing but may be useful in cancer therapy since they only integrate and express their genes in replicating cells. They are useful for ex vivo approaches and are attractive in this regard due to their stable integration into the target cell genome.

Adenoviruses are eukaryotic DNA viruses that can be modified to efficiently deliver a therapeutic or reporter transgene to a variety of cell types. The general adenoviruses types 2 and 5 (Ad2 and Ad5, respectively), which cause respiratory disease in humans, are currently being developed for gene therapy of Duchenne Muscular Dystrophy (DMD) and Cystic Fibrosis (CF). Both Ad2 and Ad5 belong to a subclass of adenovirus that are not associated with human malignancies. Adenovirus vectors are capable of providing extremely high levels of transgene delivery to virtually all cell types, regardless of the mitotic state. High titers ($10^{13}$ plaque forming units/ml) of recombinant virus can be easily generated in 293 cells (an adenovirus-transformed, complementation human embryonic kidney cell line: ATCC CRL1573) and cryo-stored for extended periods without appreciable losses. The efficacy of this system in delivering a therapeutic transgene in vivo that complements a genetic imbalance has been demonstrated in animal models of various disorders. See Y. Watanabe, *Atherosclerosis*, 36: 261–268 (1986); K. Tanzawa et al, *FEBS Letters*, 118(1): 81–84 (1980); J. L. Golasten et al, *New Engl.J. Med.*, 309 (11983): 288–296 (1983); S. Ishibashi et al, *J. Clin. Invest.*, 92: 883–893 (1993); and S. Ishibashi et al, *J. Clin. Invest.*, 93: 1889–1893 (1994), all of which are incorporated herein by reference. Indeed, recombinant replication defective adenovirus encoding a cDNA for the cystic fibrosis transmembrane regulator (CFTR) has been approved for use in at least two human CF clinical trials. See, e.g., J. Wilson, *Nature*, 365: 691–692 (Oct., 21, 1993). Further support of the safety of recombinant adenoviruses for gene therapy is the extensive experience of live adenovirus vaccines in human populations.

Human adenoviruses are comprised of a linear, approximately 36 kb double-stranded DNA genome, which is divided into 100 map units (m.u.), each of which is 360 bp in length. The DNA contains short inverted terminal repeats (ITR) at each end of the genome that are required for viral DNA replication. The gene products are organized into early (E1 through E4) and late (L1 through L5) regions, based on expression before or after the initiation of viral DNA synthesis. See, e.g., Horwitz, Virology, 2d edit., ed. B. N. Fields, Raven Press Ltd., New York (1990).

The adenovirus genome undergoes a highly regulated program during its normal viral life cycle. Y. Yang et, al *Proc. Natl. Acad. Sci., U.S.A*, 91: 4407–4411(1994). Virions are internalized by cells through as yet unidentified receptors, enter the endosome, and from there the virus enters the cytoplasm and begins to lose its protein coat. The virion DNA migrates to the nucleus, where it retains its linear structure rather than integrating into the chromosome.

The immediate early genes, E1a and E1b, are expressed in the nucleus. These early gene products regulate adenoviral transcription and are required for viral replication and expression of a variety of host genes (which prime the cell for virus production), and are central to the cascade activation of early delayed genes (e.g. E2, E3, and E4) followed by late genes (e.g. L1–L5).

The first-generation recombinant, replication-deficient adenoviruses which have been developed for gene therapy of DMD and other inherited disorders contain deletions of the entire E1a and part of the E1b regions. This replication-defective virus is grown in 293 cells containing a functional adenovirus E1a gene which provides a transacting E1a protein. E1-deleted viruses are capable of replicating and producing infectious virus in the 293 cells, which provide E1a and E1b region gene products in trans. The resulting virus is capable of infecting many cell types and can express the introduced gene (providing it carries its own promoter), but cannot replicate in a cell that does not carry the E1 region DNA unless the cell is infected at a very high multiplicity of infection. Adenoviruses have the advantage that they have a broad host range, can infect quiescent or terminally differentiated cells such as neurons, and appear essentially non-oncogenic. Adenoviruses do not appear to integrate in to the host genome. Because they exist extrachromasomally, the risk of insertional mutagenesis is greatly reduced. Ali et al., supra, at 373. Recombinant adenoviruses (rAdV) produce very high titers, the viral particles are moderately stable, expression levels are high, and a wide range of cells can be infected. Their natural host cells are airway epithelium, so they are useful for therapy of lung cancers.

Adeno-associated viruses (AAV) have also been employed as vectors for somatic gene therapy. AAV is a small, single-stranded (ss) DNA virus with a simple genomic organization (4.7 kb) that makes it an ideal substrate for genetic engineering. Two open reading frames encode a series of rep and cap polypeptides. Rep polypeptides (rep78, rep68, rep 62 and rep 40) are involved in replication, rescue and integration of the AAV genome. The cap proteins (VP1, VP2 and VP3) form the virion capsid. Flanking the rep and cap open reading frames at the 5' and 3' ends are 145 bp inverted terminal repeats (ITRs), the first 125 bp of which are capable of forming Y- or T-shaped duplex structures. Of importance for the development of AAV vectors, the entire rep and cap domains can be excised and replaced with a therapeutic or reporter transgene. See B. J. Carter, in Handbook of Parvoviruses, ed., P. Tijsser, CRC Press, pp. 155–168 (1990). It has been shown that the ITRs represent the minimal sequence required for replication, rescue, packaging, and integration of the AAV genome.

The AAV life cycle is biphasic, composed of both latent and lytic episodes. During a latent infection, AAV virions enter a cell as an encapsidated ssDNA, and shortly thereafter are delivered to the nucleus where the AAV DNA stably integrates in to a host chromosome without the apparent need for host cell division. In the absence of a helper virus, the integrated AAV genome remains latent but capable of being activated and rescued. The lytic phase of the life cycle begins when a cell harboring an AAV provirus is challenged with a secondary infection by a herpes virus or adenovirus which encodes helper functions that are recruited by AAV to aid in its excision from host chromatin (B. J. Carter, supra). The infecting parental ssDNA is expanded to duplex replicating form (RF) DNAs in a rep dependent manner. The rescued AAV genomes are packaged into preformed protein capsids (icosahedral symmetry approximately 20 nm in diameter) and released as infectious virions that have packaged either + or − ssDNA genomes following cell lysis.

Adeno-associated viruses (AAV) have significant potential in gene therapy. The viral particles are very stable and recombinant AAVs (rAAV)have "drug-like" characteristics in that rAAV can be purified by pelleting or by CsCl gradient banding. They are heat stable and can be lyophilized to a powder and rehydrated to full activity. Their DNA stably integrates into host chromosomes so expression is long-term. Their host range is broad and AAV causes no known disease so that the recombinant vectors are non-toxic.

In a specific embodiment of a gene therapy method (Example 1) mutant E2F1 proto-oncogenes are directed into RB (−/−) tumor cells using plasmids encoding E2F1 mutant oncoproteins. Transfection of genes encoding these mutant oncoproteins can induce a significant growth blockage effect in these human tumor cells. The mutant oncoproteins are stably expressed and, in those cells, the cell morphology changes to a form that mimicks cell senescence.

Furthermore, mutant proto-oncogenes may also be introduced into a target cell using a variety of well-known methods that use non-viral based strategies that include electroporation, membrane fusion with liposomes, high velocity bombardment with DNA-coated microprojectiles, incubation with calcium-phosphate-DNA precipitate, DEAE-dextran mediated transfection, and direct microinjection into single cells. For instance, a mutant proto-oncogene may be introduced into a tumor cell by calcium phosphate coprecipitation (Pillicer et al., *Science*, 209: 1414–1422 (1980); mechanical microinjection and/or particle acceleration (Anderson et al., *Proc. Nat. Acad. Sci. USA*, 77: 5399–5403 (1980); liposome based DNA transfer (e.g., LIPOFECTIN-mediated transfection- Fefgner et al., *Proc. Nat. Acad. Sci., USA*, 84: 471–477 (1987), Gao and Huang, Biiochem. Biophys. Res. Comm., 179: 280–285, 1991); DEAE Dextran-mediated transfection; electroporation (U.S. Pat. No. 4,956,288); or polylysine-based methods in which DNA is conjugated to deliver DNA preferentially to liver hepatocytes (Wolff et al., *Science*, 247: 465–468 (1990), Curiel et al., *Human Gene Therapy* 3: 147–154 (1992). Each of these methods is well represented in the art. Moreover, plasmids containing mutant proto-oncogenes may placed into tumor cells using many of these same methods.

Once introduced into a target cell, mutant proto-oncogene sequences can be identified by conventional methods such as nucleic acid hybridization using probes comprising sequences that are homologous/complementary to the inserted mutant proto-oncogene sequences of the vector. In another approach, the sequence(s) may be identified by the presence or absence of a "marker" gene function (e.g, thymidine kinase activity, antibiotic resistance, and the like) caused by introduction of the expression vector into the target cell. For instance, if a polynucleotide encoding a mutant E2F proto-oncogene transcription factor is inserted into a vector having a dominant selectable marker gene such as a neomycin phosphotransferase gene under separate control of an SV40 early promoter, the sequence can be identified by the presence of the marker gene function (Geneticin resistance). Other methods of detecting the appropriate vector (e.g., PCR methods) will be readily available to a worker of ordinary skill in the art.

The effect of transfection with mutant proto-oncogenes may be tested in vitro using any one of a number of readily available human tumor cell lines. Such cell line include an RB-defective human bladder carcinoma cell line, 5637 (ATCC HTB9), an RB-defective human breast carcinoma cell line, MDA-MB-468 (ATCC HTB132); an RB-defective human prostate carcinoma cell line, DU145 (ATCC HTB81); an RB-defective human osteosarcoma cell line, SAOS2 (ATCC HTB85); an RB-defective human fibrosarcoma metastatic to lung cancer cell line, Hs913T (ATCC HTB152). Each of these cell lines may be transfected with the appropriate mutant proto-oncogenes and the effect of transfection on cell growth and cellular morphology may be tested using procedures described herein. See Example 1.

A tumor cell containing the mutant proto-oncogene may also be used in assays for mutagenic or tumorigenic materials. A tumor cell that has stopped growing as the result of transfection using a mutant proto-oncogene (i.e., SEQ ID NO. 4) is challenged with a material (i.e., a drug) suspected of being mutagenic. The effect of the material on overcoming the growth inhibitive effects of the mutant oncogene is measured as described, for instance, in Example 1 by assaying cell growth parameters.

Tumor cells containing a polynucleotide sequence encoding a mutant oncoprotein may also be used to isolate new genes. We have shown (See Example 1) that, while most SAOS2 cells transfected with our mutants died, some survived to form colonies. (See Table III, infra) Those surviving cells displayed an altered morphology (cell shrinkage). It is likely that these surviving cells have mutated or induced an unknown cellular gene which allows survival even in the presence of the dominant interfering mutant of E2F1. These surviving cells may be used for isolating the genes which are responsible for inducing the altered phenotype. For isolation of these genes, standard subtractive hybridization technology is used. See Ausubel et al., Current Protocols in Molecular Biology, unit 5.8B, incorporated herein by reference. Briefly, subtracted hybridization produces a cDNA library which contains cDNA clones corresponding to only those mRNAs present in the stable tumor cell lines expressing E2F mutant oncoproteins and not present in the parental tumor cells or cell lines which contain the vector lacking the mutant E2F sequences. To this end, mRNAs from stable cell lines expressing mutant E2F oncoproteins are converted into cDNAs and are designated as (+). The mRNAs from the parental cell line or the vector cell lines are similarly converted to cDNAs and are designated (−). "Positive" (+) cDNA with restriction enzyme (EcoR1) ends and "negative" (−) cDNA with blunt ends are prepared. The (−) cDNA may be digested with blunting enzymes such as Rsa1 and Alu1 to give blunt-ended fragments. The (+) cDNA inserts are mixed with a 50-fold excess of fragmented (−) cDNA inserts, the DNAs in the mixture are heated to melt the double-stranded DNA, and the single stranded insert DNA is allowed to hybridize. After hybidization, annealed cDNA inserts are ligated into an amplification vector such as lambda gt11 with EcoR1 as arms. The only (+) cDNA likely to regenerate double-stranded fragments with an EcoR1 site at each end are those sequences for which no complementary fragments were present in the (−) cDNA (i.e., cDNA clones corresponding to only those mRNAs present in the stable tumor cell lines expressing E2F mutant oncoproteins and not present in the parental tumor cells or cell lines). Subsequently, those sequences are amplified and sequenced and may also be used further as probes to extract the full-length cDNA clones in the original cDNA library. The full-length cDNAs are sequenced using standard procedures. Isolated cDNA is then screened for the presence of an ability to render SAOS2 cells resistant to the activity of our mutant oncoproteins. Genes having this ability are useful in in vitro assays to test or screen anti-cancer drugs. In particular, the effects of cellular toxicity and/or bioavailability of a test drug can be generally ignored in an in vitro system, the assay directed to the effect of the anti-cancer drug on, for instance, the binding affinity of the isolated gene/gene product or on the change in enzymatic properties of the molecular target.

B. Formulations. Pharmaceutically acceptable carriers containing an effective amount of mutant proto-oncogene sequence or mutant oncoprotein sequence may be administered intraocularly, parenterally, orally, intranasally, intravenously, intramuscularly, subcutaneously, or by other means. The term "pharmaceutically acceptable carrier" means one or more organic or inorganic ingredients, natural or synthetic, with which the mutant proto-oncogene or mutant oncoprotein is combined to facilitate its application. A suitable carrier includes sterile saline although other aqueous and non-aqueous isotonic sterile solutions and sterile suspensions known to be pharmaceutically acceptable are known to those of ordinary skill in the art. In this regard, the term "carrier" encompasses liposomes and the HIV-1 tat protein (See Pepinsky et al., supra) as well as any plasmid and viral expression vectors. An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

In preferred methods, an effective amount of the mutant proto-oncogene sequence contained within its attendant vector (i.e., "carrier) may be directly administered to a target cell or tumor tissue via direct injection with a needle or via a catheter of other delivery tube placed into the cancer or tumor. Dosages will depend primarily on factors such as the condition being treated, the selected mutant proto-oncogene, the age, weight, and health of the subject, and may thus vary among subjects. An effective amount for a human subject is believed to be in the range of about 0.1 to about 50 ml of saline solution containing from about $1\times10^7$ to about $1\times10^{11}$ plaque forming units (pfu)/ml mutant proto-oncogene containing, viral expression vectors.

Target cells treated by mutant proto-oncogenes may be administered topically, intraocularly, parenterally, intranasally, intratracheally, intrabronchially, intramuscularly, subcutaneously or by any other means. Target cells to be treated by oncoprotein may be administered topically, intraocularly, parenterally, intranasally, intratracheally, intrabronchially, intramuscularly, subcutaneously or by any other means.

In vivo testing of dominant interfering mutants in an animal model is conveniently accomplished. Tumors are formed in nude mice by injecting RB (−/−) human tumor cell lines into the mice. The nude mice are immunodeficient (reference?) and will not reject the foreign tumor cells. Tumors form 1–2 weeks after tumor cell injection although the exact timing depends upon the number of cells injected and the tumorigenicity of the cell lines. Mutant proto-oncogene polynucleotides expressing dominant interfering mutants of, for example, E2F transcription factors are introduced into the tumor cells by conventional transfection procedures in culture prior to injection into the mice. Alternately, the appropriate mutant proto-oncogene polynucleotide may be introduced into the tumor by transfection or viral transduction in vivo after the tumors have formed in the mice.

The cells used are either the bladder carcinoma cell line HTB9 (Huang et al., supra) or the retinoblastoma cell line WERI-Rb27 (both Takahashi et al., *Proc. Nat. Acad. Sci. USA* 88:5257–5261, 1991, incorporated herein by reference.

For delivery of the mutant proto-oncogene in culture, tumor cells are transfected (using a conventional procedure such as calcium phosphate precipitation, electroporation, or lipofectamine transfection) or directly infected (using a retrovirus, adenovirus, or adeno-associated virus. In the case of an efficient viral infection in which 100% of cells have successfully incorporated the appropriate mutant proto-oncogene, no selection of cells is required. In the case of transfections which are not as efficient as viral infections, cells are transfected with an expression vector encoding both a drug-resistance gene (such as the neo gene which encodes G418 resistance) and a mutant proto-oncogene such as SEQ ID NOS. 4–5. A control transfection is a vector encoding the drug-resistance gene alone.

After about 2–3 weeks of selection in the drug-containing media, the cell colonies are pooled and subcutaneously injected into the flank of nu/nu (nude) female mice at a cell number ranging from about $10^6$ to about $10^7$ in a volume of about 100 ul. Virus-infected cells are injected directly without the need for a selection step. The mice are further maintained for at least two months and tumor size is monitored on a weekly basis using calipers.

Alternately, untransfected or uninfected tumor cells are subcutaneously injected in the flank of the mice. After several weeks of tumor formation, DNA or virus containing a polynucleotide encoding a dominant interfering mutant of, for example, an E2F1 transcription factor, are surgically injected into the tumors of certain mice. Many viruses are suitable for this procedure, although recombinant adenoviruses are the most efficient and recombinant retroviruses have the advantage of being stably integrated into the tumor cell genome. DNA can be introduced into the cells by mixing the DNA with cationic liposomes and injecting the mixture. See Example 2. DNA or viruses not containing the mutant proto-oncogene are injected into tumors of other mice to serve as the control. Tumor progression or reduction is monitored with calipers. A dominant interfering mutant of an E2F transcription factor is expected to inhibit tumorigenesis by these RB(−/−) cells, while vector lacking an insert or expressing wild-type E2F transcription factor would not.

As a further example, treatment of human small cell lung carcinoma with liposome-encapsulated, isolated mutant oncoprotein may be performed in vivo by introducing a mutant oncoprotein into cells in need of such treatment using liposomes, in particular small-particle liposome aerosols. Administered via aerosols, mutant oncoprotein is deposited uniformly on the surface of the nasopharynx, the tracheobronchial tree and in the pulmonary area. See, Knight and Gilbert, *Eur. J. Clin. Micro. and Infect. Dis.*, 7: 721–731 (1988), incorporated herein by reference, for discussion of liposome aerosols. To treat lung cancers in this way, the mutant oncoprotein is purified, for example, from recombinant—infected CHO cells by immunoaffinity chromatography or any other convenient method. The mutant oncoprotein is mixed with liposomes (See Example 2) and incorporated into them at high efficiency. The encapsulated oncoprotein may be tested in vitro for any effect on inhibiting cell growth by the methods described in Example 1. Since the aerosol delivery is mild and well-tolerated by normal volunteers and patients, the mutant oncoprotein-containing liposomes are administered to treat patients suffering from lung cancers of any stage. The liposomes are delivered by nasal inhalation or by an endotracheal tube connected to a nebulizer at a dose sufficient to inhibit tumor growth. Aerosolization treatments are administered daily for two weeks, with repetition as needed.

In vivo studies using orthotopic small cell lung carcinoma may be carried out using cells which lack functional (RB+)

expression. These cells are injected into the right mainstream bronchus of athymic (nu/nu) nude mice (about 1.5× $10^6$ cells per mouse). Three days later, the mice begin a course of treatment (daily for three consecutive days) of being inoculated endobronchially with supernatant from retrovirus producer cells containing mutant E2F1 proto-oncogene polynucleotide sequences or supernatant from retrovirus producer cells containing the wild-type E2F1 proto-oncogene polynucleotide sequences. Tumor formation and size are followed in both treatments by measurement with calipers.

The following examples are illustrative but are not intended limit in any way the scope of the invention.

EXAMPLE 1
Inhibition of Tumor Growth Using E2F1 Mutants
Materials and Methods

Procedures for developing plasmids containing mutant E2F1 proto-oncogenes are described in Qin et al., *Mol. Cell. Biol.*, 15- 742–755 (1995)incorporated herein by reference. One mutant proto-oncogene was designed to be a dominant mutant which interferes with E2F1 function at the level of protein interaction. This mutant proto-oncogene sequence ("E2F1b" or "E2F1 (d153+d118)": Qin et al., 1995, supra) is shown in SEQ ID NO.: 5 and its deduced amino acid sequence is shown in SEQ ID NO.: 10. E2F1b lacks the DNA binding motif (amino acids 128 to 191 of wild type E2F1 SEQ ID NO.: 1) and the RB-binding domain (amino acids 409 to 426 of wild-type E2F1), but contains the "marked" box (amino acids 251 to 317 of wild-type E2F1) and the leucine zipper sequence (amino acids 215 to 243 of wild-type E2F1). Briefly, the E2F1 cDNA encoding wild-type "RBAP-1" from plasmid pSP72-RBAP-1 (see Kaelin et al., supra, incorporated herein by reference) is excised by partial digestion with BamHI and BglII and subcloned into the BamHI site of pSG5 (Stratagene, La Jolla, Calif.). The plasmid pSG5-E2F1b (d118+d153) is constructed by site-specific single-strand mutagenesis, using the Bio-Rad Mutgene kit as directed, SEQ ID NO.: 11 and SEQ ID NO.: 12 as primers, and pSG5-E2F1 grown in *Escherichia coli* CJ236 as the template.

Another mutant proto-oncogene was designed to compete with endogenous wild-type E2F1 for DNA binding. We developed an E2F1 N-terminal fragment which contains the DNA-binding domain (see above) but lacks the known transactivation and RB-binding domains (amino acids 197 to 437 of wild-type E2F1). This mutant SEQ ID NO.: 4 ("E2F1a" or "E2F1(1-196)"; Qin et al., 1995,supra) is made as follows:

The HindIII-SmaI E2F1 cDNA fragment from plasmid pSP72-RBAP-1 containing wild-type "RBAP-1" (Kaelin et al., supra) is ligated into the backbone DNA fragment generated by digesting plasmid pSP72-E2F1 (bHlH) containing the E2F1 cDNA corresponding to the basic helix-turn-helix (HLH) region (amino acid 89 to 95; see Krek et al., *Science*, 262: 1557, 1993, incorporated herein by reference) with HindIII and SmaI. The E2F1a (amino acid 1-196) insert is excised as a BamHI-BglII fragment and then subcloned to the BamHI site of the pSG5 vector (Stratagene).

Cell Culture, Transfections

SAOS2 human osteosarcoma RB(−/−) cells (ATCC HTB85) are grown in Dulbecco's modified Eagle's medium (Sigma) with 10% heat-inactivated HyClone bovine serum at 37° C. The transfection procedure is a calcium phosphate method in which cells were transfected at 90% confluence. Briefly, 20 micrograms of plasmid DNA are used in the method of De Caprio et al., *Cell* 54: 275–283 (1988), incorporated herein by reference. The medium is changed twice, 16 hr after transfection.

Expression vectors encoding E2F1 mutants are co-transfected along with a CD19 encoding plasmid (provided by T. Tedder). We know that SAOS2 cells do not express detectable CD19 and synthesis of CD19 alone does not affect the normal distribution of theses cells in the cell cycle (data not presented). The CD19 marker is used here as a way of identifying those SAOS2 cells that have been successfully transfected in the transient transfection assay. Transient expression of the E2F1 mutant in these cells should lead to G1 arrest.

For growth assays, SAOS2 cells are stably transfected with about 20 μg of plasmid containing a neo marker gene and the appropriate E2F1 mutant proto-oncogene sequences. For colony growth assays, the cell growth medium is supplemented with G418 (300 μg/ml) 48 h after transfection. About three weeks after G418 selections, colonies are stained with Crystal Violet and assayed under light microscopy.

Western Blotting (Immunoblotting) and Immunofluorescence.

The Western blotting and immunofluorescence experiments are performed as described previously by Qin et al., supra. The antibodies against E2F-1 are a rabbit polyclonal antibody, P98 (Kaelin et al., *Cell*, 70: 351 (1992)). P98 (1:200 dilution) is used in the immunofluorescence staining studies. The subcellular location of wild type E2F-1 and E2F-1 mutants is determined by indirect immunofluorescence staining by using a fluorescein isothiocyanate (FITC) -conjugated goat anti-rabbit immunoglobulin G secondary antibody (Boehringer Mannheim) after transfection of the plasmids encoding the various oncoproteins. Following fixation with 1.5% paraformaldehyde, cells are permeabilized by immersion in phosphate-buffered saline (PBS) containing 0.3% Triton X-100 for 5 min and stained for E2F-1. E2F-1 antibody is visualized through the use of a rhodamine-conjugated anti-rabbit second antibody (Boehringer).

Flow Cytometric Analysis.

SAOS2 cells are transfected with indicated plasmid combinations (plasmids containing various E2F1 mutants and CD19 encoding plasmid). Three days after transfection, the cells are subjected to CD19 immunofluorescence staining and propidium iodide staining for DNA. About 2 μg of the CD19-encoding plasmid and 20 μg of E2F-1-encoding plasmids are present in each transfection mixture. The cells are trypsinized, washed with PBS containing 0.1% bovine serum albumin and 20 mM N-2 hydroxyethylpiperazine-N'-2-ethanesulfonic acid (HEPES; pH 7.3), and then reacted with a primary (anti-CD19) antibody (CD19.15; 1:500 dilution) for 1 h on ice. The cells are then washed an incubated with a secondary antibody (FITC-conjugated goat anti-mouse)(15 μg/ml; Boehringer) for 40 min on ice. The cells are washed again and then fixed in pre-cooled 70% ethanol at 4° C. overnight. Prior to sorting, the cells are washed again and then treated with an RNase A (5 μg/ml) and propidium iodide solution (69 μM propidium iodide, 38 mM sodium citrate) for 20 min at 37° C.

Flow cytometry analysis (fluoroscence-activated cell sorting: FACS) is then performed as described by Qin et al., supra. Briefly, samples of cells having undergone a transient transfection are analyzed by flow cytometry on a Becton-Dickinson FACScan. Transfection of the CD19 surface marker identifies those cells that are successfully transfected. The CD19 negative control consists of transfections lacking a CD19 plasmid. About 2–3×$10^4$ cells per sample are analysed. FACS analysis is performed in which CD19 positive cells are counted as those cells with an FITC fluorescence staining intensity that is greater than that of the cells in the negative controls. The cell population at the different stages of the cell cycle are determined by the propidium iodide-staining intensity of the DNA. Cells having 2N and 4N DNA content are clearly distinguishable. G1/G0 cells are those with a 2N content. The percentage of cells in the G1/G0 phase is determined for all transfectants.

RESULTS

Transfection of mutant E2F1 proto-oncogene polynucleotides into tumors lacking a functional RB gene [RB(−/−)] leads to a reproducible G1/G0 arrest, manifested by a ~30% net increase of CD19-positive G1/G0 cells over the number observed in the vector-transfected control population. Table II shows the percentage of cells in G1/G0 and the increase in percentage of cells in G1/G0 as compared to the control transfection (expression vector lacking insert).

TABLE II

| Transfection | G1 Cells | Increase in % of cells in G1/G0 |
|---|---|---|
| EXPERIMENT 1 | | |
| pCD19 Control DNA | 48% | 0 |
| pCD19 pSG3E2F1a (SEQ ID NO.: 4) | 76.0% | 28.0% |
| pCD19 pSG5E2F1b (SEQ ID NO.: 5) | 72.8% | 24.8% |
| pCD19 pSG5RB (wild-type RB) | 77.3% | 29.3% |
| pCD19 pSG5E2F1 (SEQ ID NO.: 1) | 42.0% | −6.0% |
| EXPERIMENT 2 | | |
| pCD19 Control DNA | 29.3% | 0 |
| pCD19 pSG5E2F1a | 51.4% | 22.1% |
| pCD19 pSG5E2F1b | 58.8% | 29.5% |
| pCD19 pSG5RB | 60.5% | 31.2% |
| pCD19 pSG5E2F1 | 36% | 6.7% |

Data from these two experiments is summarized in FIG. 1, plotting the percentage increase in G1/G0. For instance, if the vector control showed an average of 50% G1/G0 cells and the E2F1a transfection showed an average of 80% cells in G1/G0, the increase in G1/G0 is 30%. As can be seen, transfection of the E2F mutant proto-oncogenes leads to a significant increase in the percentage of cells in G1/G0 as compared to transfection with wild type E2F1 and the control treatments. This clearly demonstrates growth inhibition by the mutants. The level of inhibition is roughly equivalent to that produced by wild-type RB transfection ("pSG5RB"). Western blot analysis also suggests that E2F1 level is high in these tumors. (data not presented)

We examined whether the expression of E2F1 mutants is compatible with tumor cell growth, by co-transfecting plasmids encoding each of the E2F1 mutants into these osteosarcoma cells with pCMV-Neo-Bam (obtained from Dr. B. Vogelstein), a plasmid expressing the G418-resistance gene. Cells are further maintained in G418-containing medium for three weeks and stained for colony formation with crystal violet solution. The colony growth assay (TABLE III) shows that SEQ ID NO.: 4 (E2F1a) significantly inhibits colony formation while SEQ ID NO.: 5 (E2F1b) exhibits a less dramatic effect.

TABLE III

COLONY GROWTH INHIBITION EFFECT BY E2F1 MUTANTS

| Transfection | Colony Number |
|---|---|
| pSG5 (control) pCMV-Neo-Bam | 258 |
| pSG5E2F1a (SEQ ID. 4) pCMV-Neo-Bam | 15 |
| pSG5E2F1b (SEQ ID. 5) pCMV-Neo-Bam | 85 |

Moreover, stable cells expressing SEQ ID NO.: 4 exhibit shrinking cell morphology while cells stably expressing SEQ ID NO.: 5 exhibit a flat morphology mimicking senescence, similar to the morphology observed upon introduction of RB into these cells (data not shown).

Figure 2:
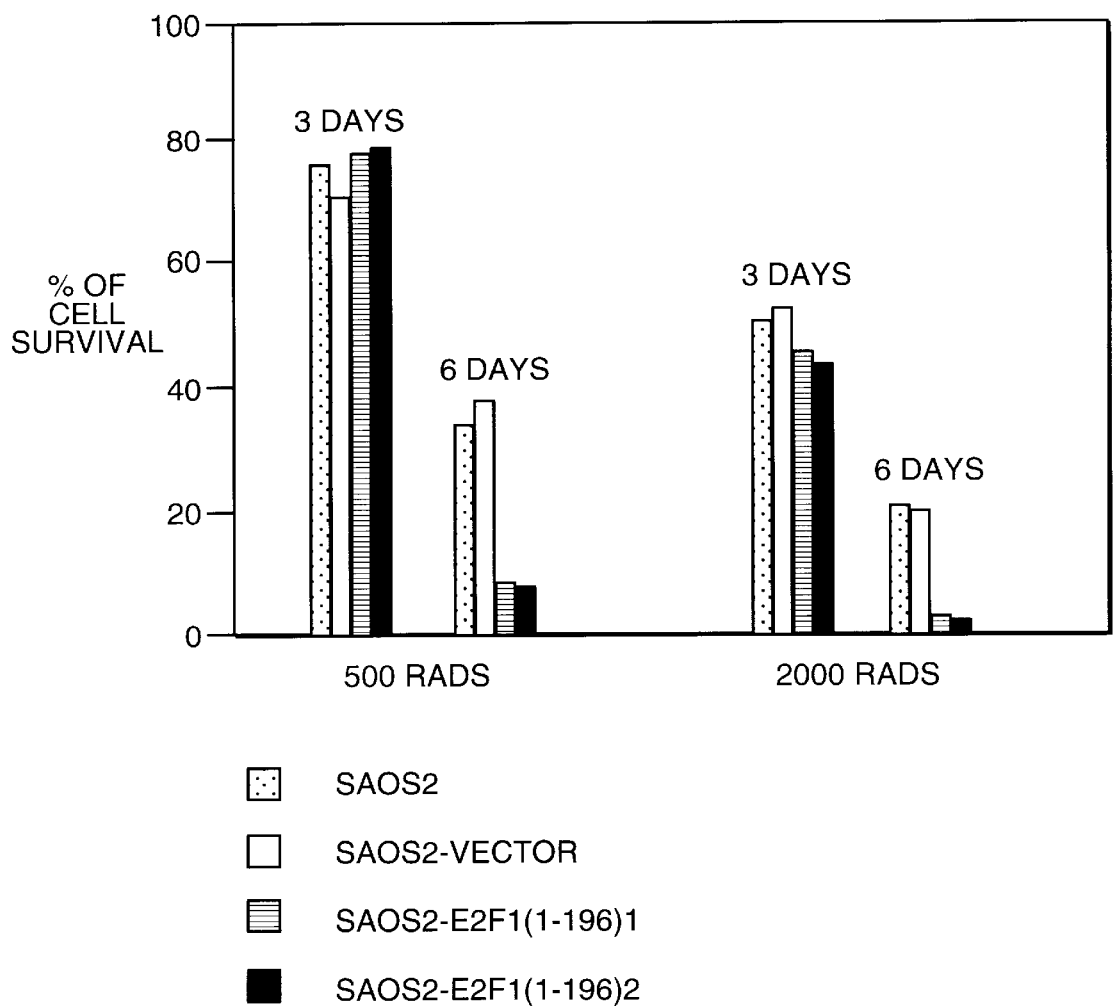
FIG. 2 is a bar graph plotting the percentage of cell survival of the parental tumor cells, tumor cells transfected with a control plasmid and tumor cells expressing two separate "E2F1a" mutants (SEQ ID NO.: 4) after 2 different doses of X-ray. "Day 3" and "day 6" are post-X ray treatment follow-ups.

Clearly, some cells survive transfection with our E2F mutants. We tested the responsiveness of the surviving cells by taking equal amounts ($1.2 \times 10^5$ cells) of SAOS2 parental cells, SAOS2 vector cells, and two different SAOS2 E2F1a (SEQ ID NO.: 4) clones, and irradiating them with X-rays are two different dosages (500 rads and 2000 rads). Three and six days after irradiation, cells are trypsinized, incubated with Trypan Blue, and counted with a hemacytometer under the light microscope. The percentage of cell survival is measured by dividing cell number after irradiation with the cell number before irradiation. Significantly, FIG. 2 illustrates that stable cell lines expressing E2F1a (SEQ ID NO.: 4) also exhibit much higher sensitivity to X-ray treatment than cells lines transfected with a control plasmid ("SAOS2-plasmid") or the parental cell lines ("SAOS2"). This Figure illustrates that we have, in effect, developed a method of sensitizing tumor cells to an environmental insult, such as X-ray irradiation. Tumor cells that survive transfection with our E2F mutants are more prone to damage by X-ray irradiation than non-transfected tumor cells. Thus, a multi-step approach to killing of RB (−/−) tumor cells may be accomplished by first providing to a target cell, according to the methods of this invention, an isolated, mutant proto-oncogene. The mutant proto-oncogene, upon expression, will encode for a mutant oncoprotein that is capable of inhibiting growth of the target cell. Cells that survive treatment with the mutant proto-oncogene are then challenged with an environmental insult. Preferably, the insult is designed to affect the genetic stability of the tumor cells. Such insults may include application of a variety of immunotherapeutics (e.g., monoclonal antibodies and fragments thereof), cellular response modifiers (e.g., various interleukins, cytokines, lymphokines and the like). Gamma and X-ray irradiation are the most preferred encironmental insults.

DISCUSSION

Dominant interfering mutants of the E2F family of onco-proteins may selectively inhibit the transformed phenotype of RB (−/−) tumor cells which exhibit elevated levels or activity of the corresponding proto-oncogenes, while leaving other cells unaffected. For example, normal proliferating cells are RB(+). In these cells, E2F1 and RB form complexes along with other cellular proteins. See, Krek et al., supra, 1993. These complexes are usually stable and exhibit high binding affinity for DNA and perform transcriptional modulation at critical points of the cell cycle.

Without wishing to be bound by any theory, our dominant interfering E2F1 mutants are unlikely to affect RB-E2F transcriptional complex activity in these normal RB(+) cells since the majority of mutants lack RB-binding activity and cannot dissociate the RB:E2F complex. Also, the RB:E2F complex binds DNA with a higher affinity than E2F1 alone (Krek et al., Science 262: 1557–1560, 1993 and Helin et al., Genes Dev., 7: 1850–1861, 1993) so that our DNA binding E2F1 mutant, SEQ ID NO.: 4 (E2F1a), should not, in any event, be able to complete efficiently for DNA binding with the RB:E2F complex. Therefore, we would expect that growth of RB(+) cells is not significantly affected by our E2F1 mutants. In the case of RB(-/-) tumor cells, however, RB:E2F transcriptional complexes are necessarily absent and any excess of E2F species (such as E2F1) will continually activate transcription of its own gene and other genes (i.e., certain S-phase genes) which are required for maintaining the transformed phenotype. The E2F1 mutants interfere with E2F activity and affect the behavior of the RB (-/-) tumor cells.

Colony formation following stable transfection of our E2F1 mutants is reduced, especially in the case of E2F1a (SEQ ID NO.: 4). Most SAOS2 cells transfected with SEQ ID NO.: 4 died, some survived to form colonies. See Table III, supra. Those surviving cells displayed an altered morphology (cell shrinkage). It is possible that these surviving cells have mutated or induced an unknown cellular gene which allows survival even in the presence of the dominant interfering mutant of E2F1.

EXAMPLE 2

Preparation and Administration of Proto-Oncogene/Liposome Complex

About 0.1 ml of lactated Ringer's solution is added to a sterile vial containing plasmid DNA as SEQ ID NOS.: 4–5 (i.e., pSG5-E2F1a and pSP72-E2F1b: 20 ug/ml DNA; 0.1 ml). A 0.1 ml aliquot of this solution is added at room temperature to a separate vial containing lactated Ringer's solution and 0.1 ml of 150 uM dioleoyl phosphatidylethanolamine/3b-[N-(N',N'-dimethylaminoethane)carbomyl] cholesterol liposome (see Gao and Huang, Biochem. Biophys. Res. Comm. 179: 280–285, 1991), incorporated herein by reference. All vials are prepared according to FDA guidelines and quality control procedures. Plasmids are grown and purified in the absence of ethidium bromide or penicillin derivatives by using commercially available column chromatography methods (e.g., Promega). After incubation for 15 min at room temperature, an additional 0.5 ml of sterile lactated Ringer's solution is added to the vial and mixed. About 0.2 ml of the proto-oncogene DNA/liposome solution is injected through a 22-gauge needle into a patient's tumor.

To confirm expression of the proto-oncogene mutants in the treated tumor, core needle biopsy samples of injected tumor are obtained 3–7 days after gene transfer. Nucleic acids from the injected tumors are isolated and analysed by polymerase chain reaction using conventional methods. See, for example, Nabel et al., Proc. Acad. Nat. Sci. USA 89: 5157–5161 (1992) and Sambrook et al., A Laboratory Manual (Cold Spring Harbor Lab. Press, Plainview, N.Y., 1989), both of which are incorporated herein by reference.

EXAMPLE 3

In vivo treatment of Human Small Cell Lung Carcinoma

Small cell lung cancer patients having an endobronchial tumor accessible to a bronchoscope, and also having a bronchial obstruction, are initially selected for mutant proto-oncogene gene therapy. Treatment is administered by bronchoscopy under topical or general anesthesia. To begin the procedure, as much tumor as possible is endoscopically resected. A transbronchial aspiration needle (21 gauge)is passed through the biopsy channel of the bronchoscope. The residual tumor site is injected with the appropriate mutant proto-oncogene-expressing plasmid (See Example 1) or adenovirus suspension at a volume of about 5 to 10 ml. Protamine is added at a concentration of about 5 um/ml. Injections of therapeutic viral or plasmid supernatant comprising one or more mutant proto-oncogene expression vectors is administered around and within the tumor or tumors and into the submucosa adjacent to the tumor. Injections are repeated daily for five consecutive days and monthly thereafter. Treatment is continued as long as there is no tumor progression. After one year, the patients are evaluated to determine whether therapy should be continued. Patients wear a surgical mask for 24 hr following injection of the supernatant.

EXAMPLE 4

Treating Human Bladder Cancer

The original experimental model of human bladder cancer was established by Ahlering et al., Cancer Res., 47: 6660–6665 (1987), incorporated herein by reference. Certain human bladder cells produce local tumors only when injected by a catheter into the bladder of female nude mice. In contrast, EJ bladder carcinoma cells which were originally isolated from a more aggressive human bladder cancer produce invasive tumors in the nude mice bladders which metastasize to the lung. Ahlering et al., supra.

Tumor cells from an RB (-/-) cell line, 5637 (ATCC HTB9) are injected directly into the bladders of 6–8 week old female athymic (nu/nu) nude mice by a catheter. Ahlering et al., supra. Development and progression of the tumors are monitored using a fiberoptic system. Experimentally-induced tumors are subsequently treated with a retroviral vector (Wilson et al.,) expressing mutant E2F1 transcription factor. A vector suspension at high titer ranging from $4 \times 10^4$ to more than $1 \times 10^7$ colony forming units (CFU)/ml, and more preferably at a titer greater than $1 \times 10^6$ CFU/ml is then infused directly into the mouse bladders via a catheter. Tumor regression following vector transfer is monitored via the fiberoptic system.

All publications and patent applications mentioned are incorporated herein by reference to the same extent as if each individual publication or patent application was specifically and individually indicated to be incorporated by reference.

EQUIVALENTS

It should be understood that the preceeding is merely a detailed description of certain preferred embodiments. It therefore is apparent to those skilled in the art that various modifications and equivalents can be made without departing from the sprit or scope of the invention.

What is claimed is:

1. A composition comprising an isolated, mutant proto-oncogene that encodes a dominant interfering mutant of a transcription factor, wherein the mutant proto-oncogene comprises a polynucleotide selected from the group consisting of:
(a) SEQ ID NOS.: 4–5;
(b) a polynucleotide that hybridizes to any of the foregoing sequences under standard hybridization conditions and that encodes a protein having the cell growth inhibition activity of a dominant interfering mutant of an E2F transcription factor;
(c) a polynucleotide that encodes a protein encoded by any of the foregoing polynucleotide sequences.

2. A composition comprising a dominant interfering mutant of an endogenous nuclear transcription factor, wherein the mutant transcription factor comprises either a protein encoded by a polynucleotide selected from the group consisting of:
(a) SEQ ID NOS.: 4–5;
(b) a polynucleotide that hybridizes to any of the foregoing sequences under standard hybridization conditions and that encodes a protein having the cell growth inhibition activity of a dominant interfering mutant of an E2F transcription factor;
(c) a polynucleotide that codes on expression for a protein encoded by any of the foregoing polynucleotide sequences or comprises a selected from the group consisting of SEQ ID NOS.: 9 and 10.

3. A cell containing an isolated, mutant proto-oncogene that comprises a polynucleotide selected from the group consisting of:

(a) SEQ ID NOS.: 4–5;

(b) a polynucleotide that hybridize to any of the foregoing sequences under standard hybridization conditions and that encodes a protein having the cell growth inhibition activity of a dominant interfering mutant of an E2F transcription factor;

(c) a polynucleotide that codes on expression for a protein encoded by any of the foregoing polynucleotide sequences.

4. The cell of claim 3, wherein the cell is a tumor cell.

5. The cell of claim 4, wherein the tumor cell lacks a functioning retinoblastoma gene.

6. A cell containing an isolated, dominant interfering mutant of an endogenous nuclear transcription factor, wherein the mutant transcription factor comprises either a protein encoded by a polynucleotide selected from the group consisting of:

(a) SEQ ID NOS.: 4–5;

(b) a polynucleotide that hybridizes to any of the foregoing sequences under standard hybridization conditions and that encodes a protein having the cell growth inhibition activity of a dominant interfering mutant of an E2F transcription factor;

(c) polynucleotide that codes on expression for a protein encoded by any of the foregoing polynucleotide sequences or comprises a protein selected from the group consisting of SEQ ID NOS. 9 and 10.

7. The cell of claim 6, wherein the cell is a tumor cell.

8. The cell of claim 7, wherein the cell lacks a functioning retinoblastoma gene.

9. An expression vector comprising an isolated polynucleotide sequence selected from the group consisting of:

(a) SEQ ID NOS.: 4–5;

(b) a polynucleotide that hybridizes to any of the foregoing sequences under standard hybridization conditions and that encodes a protein having the cell growth inhibition activity of a dominant interfering mutant of an E2F transcription factor; and (c) a polynucleotide that codes on expression for a protein encoded by any of the foregoing sequences, wherein the polynucleotide sequence encodes, upon expression, a mutant E2F transcription factor.

10. The expression vector of claim 9, wherein the expression vector is selected from the group consisting of a retrovirus, an adenovirus, a herpes simplex virus, a vaccinia virus and an adeno-associated virus.

11. A cell transformed by the expression vector of claim 9.

12. A method of inhibiting growth of a tumor cell comprising administering by direct injection the expression vector of claim 9 to a cell;

expressing the mutant transcription factor in said cell in an amount effective to inhibit growth of the cell; and challenging the cell with an environmental insult.

13. The method of claim 12, wherein the step of challenging comprises challenging the cell prior to, or simultaneously with, administering the expression vector to the cell.

14. The method of claim 12, wherein the step of administering comprises administering to a tumor cell that lacks a functional retinoblastoma gene.

15. A method of sensitizing a tumor cell to an environmental insult, comprising:

providing by direct injection the expression vector of claim 9 to a tumor wherein a tumor cell containing the mutant proto-oncogene of the vector is rendered more susceptible to damage by an environmental insult than a tumor cell lacking the mutant proto-oncogene.

16. The method of claim 15, further comprising: challenging the tumor cell with an environmental insult.

17. The method of claim 16, wherein the challenging occurs at a time before the providing step or simultaneously with the providing step.

18. The method of claim 16, wherein the environmental insult is selected from the group consisting of gamma radiation and X-ray irradiation.

19. A method of making a dominant negative mutant of an endogenous, nuclear transcription factor, comprising the step of transforming a cell with the expression vector of claim 9.

20. A method of inhibiting growth of a tumor cell, comprising:

providing, by direct injection, an isolated, mutant E2F proto-oncogene to a tumor cell that lacks a functioning retinoblastoma gene, wherein the mutant E2F proto-oncogene expresses a mutant transcription factor; and wherein the tumor cell and the mutant E2F proto-oncogene are combined for a time and under conditions sufficient for said mutant E2F proto-oncogene to block growth-stimulatory action of E2F transcription factors in the absence of a functioning retinoblastoma gene.

21. The method of claim 20, wherein the step of providing comprises providing a mutant E2F proto-oncogene selected from the group consisting of (a) SEQ ID NOS.: 4–5;

(b) a polynucleotide that hybridizes to any of the foregoing sequences under standard hybridization conditions and that encodes a protein having the cell growth inhibition activity of a dominant interfering mutant of an E2F transcription factor and;

(c) a polynucleotide that codes on expression for a protein encoded by any of the foregoing sequences, wherein the polynucleotide sequence encodes, upon expression, a mutant E2F transcription factor.

22. A method of inhibiting growth of a tumor cell, comprising:

providing, by direct injection, an isolated, dominant interfering mutant of an endogenous E2F nuclear transcription factor to a tumor cell lacking a functioning retinoblastoma gene, wherein the cell is combined with the dominant interfering mutant E2F transcription factor for a time and under conditions sufficient for said mutant E2F transcription factor to block growth-stimulatory action of wild-type E2F transcription factors in the absence of a functioning retinoblastoma gene.

23. The method of claim 22, wherein the step of providing comprises providing a mutant transcription factor that comprises either a protein encoded by a polynucleotide selected from the group consisting of:

(a) SEQ ID NOS.: 4–5;

(b) a polynucleotide that hybridizes to any of the foregoing sequences under standard hybridization conditions and that encodes a protein having the cell growth inhibition activity of a dominant interfering mutant of an E2F transcription factor; and (c) a polynucleotide that codes on expression for a protein encoded by any of the foregoing polynucleotide sequences.

* * * * *